United States Patent [19]

Mark et al.

[11] 4,141,912

[45] Feb. 27, 1979

[54] PROCESS FOR THE PREPARATION OF POLYHALOBENZYLIC DISULFOOXONIUM COMPOUNDS

[75] Inventors: Victor Mark, Evansville, Ind.; Leon R. Zengierski, North Tonawanda, N.Y.

[73] Assignee: Hooker Chemicals & Plastics Corp., Niagara Falls, N.Y.

[21] Appl. No.: 840,935

[22] Filed: Oct. 7, 1977

Related U.S. Application Data

[60] Division of Ser. No. 607,326, Aug. 25, 1975, Pat. No. 4,075,238, which is a continuation of Ser. No. 410,723, Oct. 29, 1973, abandoned, which is a continuation-in-part of Ser. No. 123,014, Mar. 10, 1971, abandoned.

[51] Int. Cl.$^2$ ........................................... C07C 141/16
[52] U.S. Cl. ................................................. 260/458 C
[58] Field of Search ..................................... 260/458 C

[56] References Cited

U.S. PATENT DOCUMENTS

| | | | |
|---|---|---|---|
| 3,821,320 | 6/1974 | Mark et al. | 260/458 C |
| 3,869,491 | 3/1975 | Mark et al. | 260/458 C |

OTHER PUBLICATIONS

Mark et al., JACS, 93, 3538 (1971).

*Primary Examiner*—Nicky Chan
*Attorney, Agent, or Firm*—Peter F. Casella; William J. Crossetta, Jr.; Arthur S. Cookfair

[57] ABSTRACT

Polyhalobenzylic disulfooxonium compounds are produced by the reaction of aromatic methyl, halomethyl or hydroxymethyl substituents with sulfur trioxide. The disulfooxonium salts are readily converted to alcohols by hydrolysis to provide monomers for the production of fire resistant polymers and additives for polymers. Likewise, the disulfooxonium compounds of this invention present chemical intermediates for a wide range of useful products such as halogenated pesticides.

4 Claims, No Drawings

PROCESS FOR THE PREPARATION OF POLYHALOBENZYLIC DISULFOOXONIUM COMPOUNDS

CROSS-REFERENCE TO RELATED APPLICATION

This is a division, of application Ser. No. 607,326, filed Aug. 25, 1975 now U.S. Pat. No. 4,075,238, which is a continuation of Ser. No. 410,723, filed Oct. 29, 1973, now abandoned which is a continuation-in-part of Ser. No. 123,014, filed Mar. 10, 1971, now abandoned.

THE INVENTION

Although sulfur trioxide is recognized as a strong oxidant, it has not been used extensively due to its random reaction pattern with hydrocarbons. With paraffins and olefins, the reaction product with sulfur trioxide is a messy, intractable, dark mixture of oxidation, condensation, polymerization, sulfonation and sulfation products, demonstrating the uncontrollability of the reaction. In contrast, as an aromatic sulfonating agent and as a sulfating agent for alcohols, sulfur trioxide is used extensively, these reactions being well developed and documented.

The process of the instant invention illustrates the novel use of sulfur trioxide in oxidation and insertion reactions in the absence of uncontrollable competing reactions to afford a novel class of oxonium inner salts, the disulfooxonium type inner salts, which are completely stable but highly reactive compounds.

This invention comprises a novel class of halogenated organic compounds and methods for their preparation, said class of compounds being useful for the preparation of a variety of halogenated products, which in turn are useful as monomer precursors for polymeric systems, as additives for polymers, especially to provide fire resistance, as pesticides and as chemical intermediates. Typically, the compounds of this invention may be used to form the compounds and analogs thereof disclosed in Japanese Pat. No. 16,457; U.S. Pat. Nos. 2,621,168; 2,608,592; 2,564,214 and 2,815,301; British Pat. No. 977,961; German Patent 1,105,862; *Journal of American Chemical Society*, Vol. 71, 2756 (1949); *Journal of American Chemical Society*, Vol. 69, 1914 (1947); *Chemical Weekblad*, Vol. 9, 862 (1912) and *Industrial Engineering Chem. Prod. Res. and Dev.*, Vol 4, 259 (1965).

More particularly, this invention relates to the novel class of organic compounds properly referred to as polyhalobenzylic disulfooxonium compounds represented by the generic formula (A):

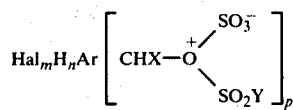

wherein

Ar is an aromatic nucleus

Hal is a halogen selected from the group consisting of fluorine, chlorine, bromine and iodine;

Y is a substituent selected from the group consisting of fluorine, chlorine, bromine and hydroxyl, provided when X is

at least one Y is hydroxy;

X is a substituent selected from the group consisting of hydrogen and

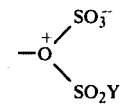

wherein Y is the same as defined above;

m, n and p are integers so selected that their sum is the number of substitutable positions available on the aromatic ring, which when Ar is benzene is six; when Ar is naphthalene is eight; when Ar is anthracene and phenanthrene and pyrene is ten.

The aromatic nucleus Ar is intended for the purposes of this disclosure to embrance the ring structures of benzene, naphthalene, anthracene, phenanthrene and pyrene. Thus, Ar is an aromatic hydrocarbon moiety of the benzene series containing from 1 to 4 six membered rings in which each substitutable hyrogen on the ring has been replaced by a halogen.

This novel class of compounds is obtainable by the reaction of the appropriate halogenated aromatic compounds with reagents containing sulfur trioxide such as neat sulfur trioxide proper, sulfuric acid solutions of SO₃ (oleum), sulfur trioxide adducts, such as those with dioxane and amines and chlorosulfonic and fluorosulfonic acids.

The following chemical equations illustrate some of these novel reactions:

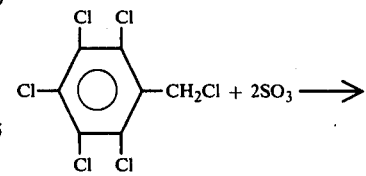

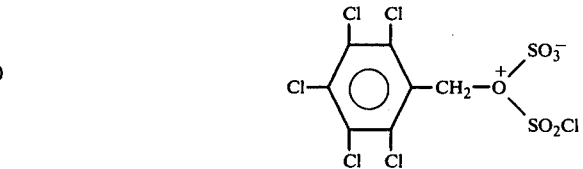

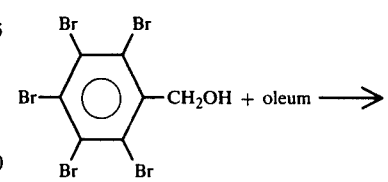

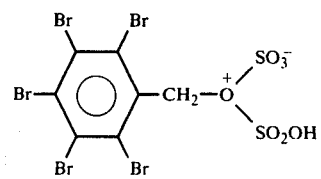

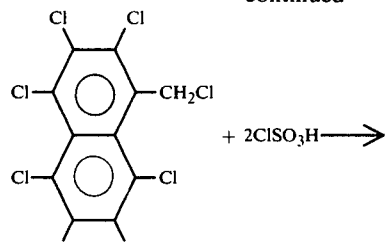

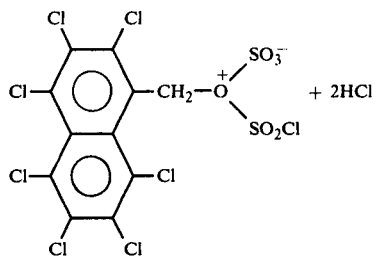

A very significant aspect of the present invention is the discovery that the reaction with sulfur trioxide and sulfur trioxide containing reagents can be carried out with concomitant oxidation of the side chain of the aromatic substrates. The significance of this finding lies in the fact that even methyl groups on the aromatic nuciei can be readily and quantitatively oxidized and transformed into products represented by generic formula A shown above with Y being hydroxy in this case. In these reactions one mole of sulfur trioxide per methyl group is used up in the oxidation step proper, yielding one mole of sulfur dioxide, as illustrated by the following reactions:

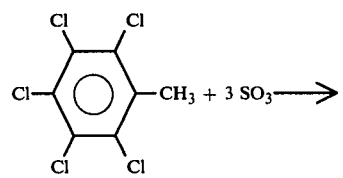

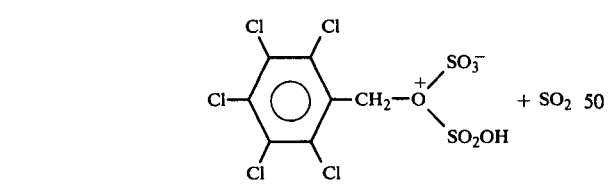

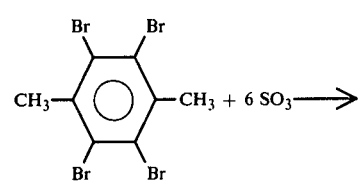

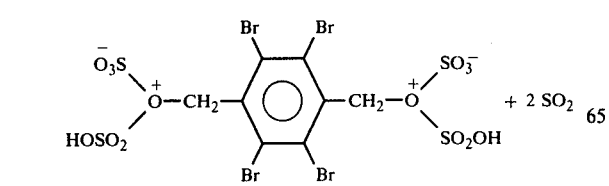

A further very useful variant of the oxidation reaction is the transformation of the methyl group into a geminal dioxonium derivative by an excess of the sulfur trioxide reagent:

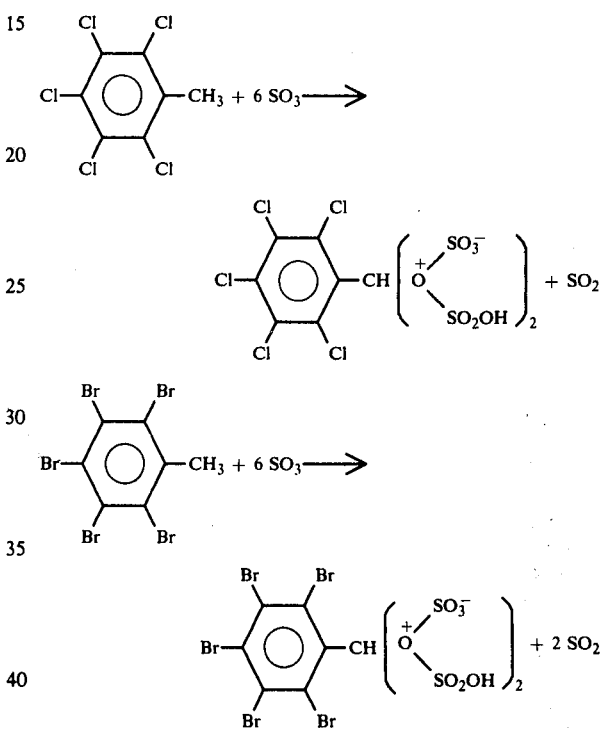

It is of considerable synthetic value that the oxidation of the methyl or substituted methyl side chains on the aromatic nuclei does not go beyond the geminal dioxonium stage even when a large excess of sulfur trioxide is used, a fact that results in subsequent transformations (vide infra) in very pure products.

The wide scope of these novel reactions is indicated by the large variety of halogenated aromatic compounds which readily undergo these transformations and yield a multitude of useful products. Derivatives of all four of the common halogens are equally suitable as starting materials, if they are present in form of mono-, di- or polynuclear aromatic compounds. The latter two classes comprise both isolated and fused ring aromatic species, some of which are listed below and in the detailed examples. All of these halogenated aromatic compounds carry one or more side chains consisting of methyl, halomethyl or hydroxymethyl substituents. As representatives of the multitude of substrates suitable for the preparation of the oxonium compounds covered by this invention the following compounds can be listed: Pentafluorotoluene, tetrafluoro-o-xylene, trifluoromesitylene, pentachlorotoluene, pentachlorobenzyl chloride, tetrachloro-m-xylene, trichloropseudocumene $\alpha,\alpha^1$,2,3,5,6-hexachloro-p-xylene, pentachlorobenzyl alcohol, heptachloro-1-methyl-naphthalene, heptachloro-2-methylnaphthalene, hexachloro-2,7-dimethyl-naphthalene, octachloro-9,10-dimethylanthracene, octachloro-4,4'-dimethylbiphenyl, pentabromotoluene, pentabromobenzyl fluoride, tetrabromo-p-xylene, 1,3,5,7-tetrabromo-2,6-dimethylnaphthalene, tribromomesitylene, dibromodurene, pentaiodotoluene, pentaiodobenzyl fluoride, tetraiodo-o-xylene, tetraiodo-m-xylene, α,α'-dichloro-2,3,5,6-tetraiodo-p-xylene, triiodomesitylene, 2-chloro-3,4,5,6-tetrabromotoluene, 2-chloro-3,4,5,6-tetraiodotoluene, 2-chloro-3,5,6-tribromo-4-iodotoluene, 2,5-dibromo-α,α',3,6-tetrachloro-p-xylene. The reactions of many of these aromatic compounds are treated in detail in the specific examples shown later.

As a result of the wide range of reactivities of both the aromatic reactants and the sulfur trioxide containing reagents a rather wide range of the desirable reaction temperatue exists. While formation of the oxonium compounds from benzylic alcohols can take place as low as −80° C., reactions involving concomitant oxidations are best carried out about 0° C., often at the boiling point of liquid SO₃, between 45° and 50° C., and with less reactive compounds, up to and in some instances about 150° C. The judicious selection of the proper SO₃ containing reagent usually obviates the use of a foreign solvent and often it is advantageous to use an excess of liquid SO₃ (which is a good solvent) or sulfuric acid (which is a liquid vehicle). A small amount (5-10%) of concentrated sulfuric acid, when added to liquid sulfur trioxide, has often a beneficial effect in increasing the rate of the oxidation of the aromatic substrate. It has been found, however, that when used in large amounts as for examaple, in the form of 20% oleum as the reaction medium, sulfuric acid can drastically alter the course of reaction as exemplified by reaction (13) (vide infra). In a few cases where needed or where beneficial, solvents not affected or not readily attacked by the sulfur trioxide species can be employed. Most often fluorinated aliphatic halocarbons, such as trichlorofluoroethane, trichlorofluoromethane and 1,1-difluorotetrachloroethane can be employed. The reactions are carried out usually at atmospheric pressure, followed if desired by the application of vacuum to recover excess liquid sulfur trioxide. When the reaction is accompanied by an oxidation step provisions should be made for the removal of the gaseous sulfur dioxide coproduct.

The structure of the oxonium compounds represented by generic formula A rests on the following:

(1) Stoichiometry of the reaction. Since most of the reactions described take place with quantitative conversion, the weight of the isolated product is indicative of its composition. When accompanied by an oxidation step, the amount of the evolved sulfur dioxide gas indicates the extent of oxidation and the number of methyl and substituted methyl groups involved.

(2) Element analysis of the product also confirms the gross composition. Because of its high reactivity and hydroscopic nature, indirect analyses, e.g. after its decomposition with water and determination of the liberated sulfuric acid and carbon, hydrogen and halogen combustion analyses, are best carried out.

(3) Nuclear magnetic resonance spectroscopy provides the best confirmation of the specific structure represented by (A) for instance the single proton nuclear magnetic resonance peak at 6.3–6.5 parts per million (ppm) downfield from the reference tetramethylsilane is compatible only with the following structure:

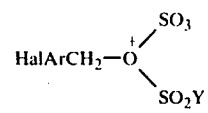

(4) The numerous reactions of the oxonium compounds, many of which take place in quantitative yield, provide also ample proof for the correctness of the molecular structure represented by generic formula (A). Representative reactions are illustrated with the pentachlorobenzyl oxonium compound:

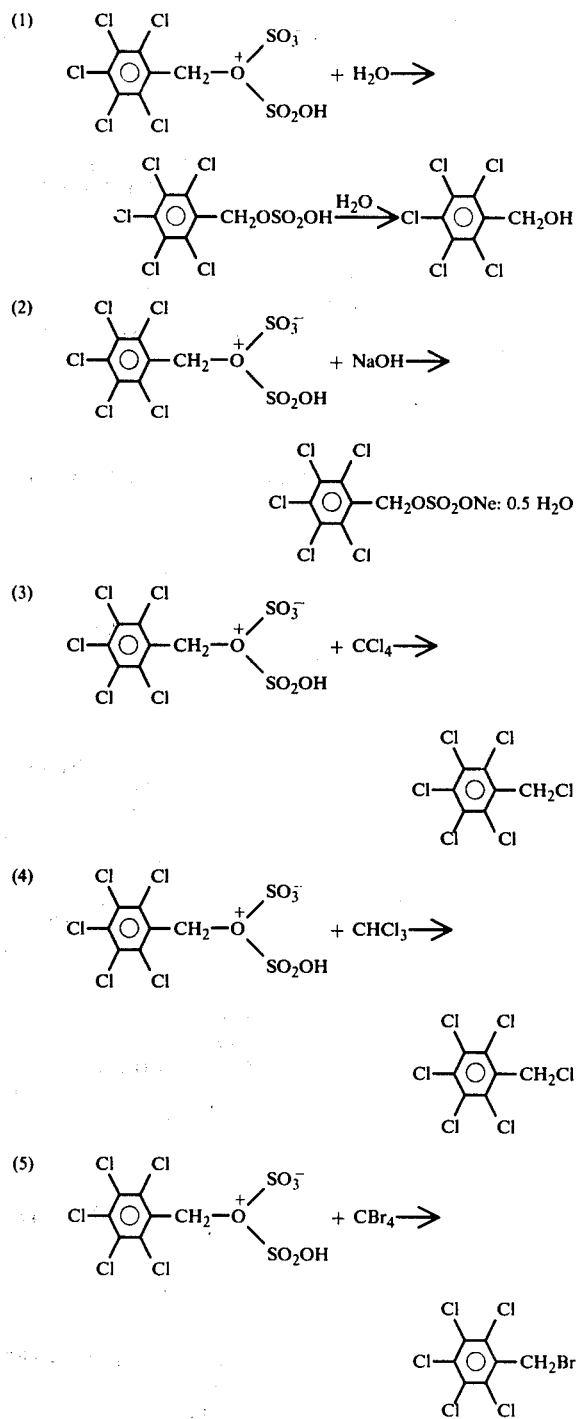

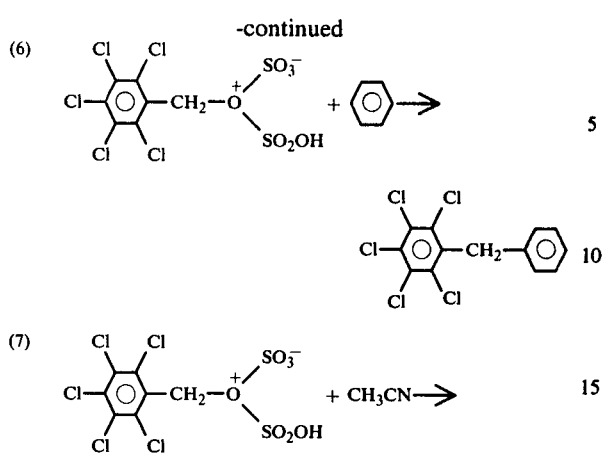
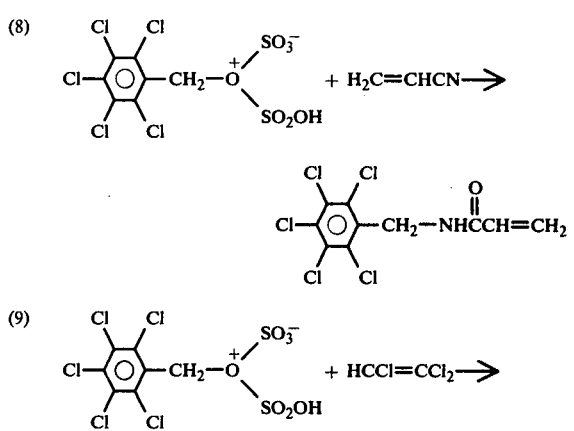
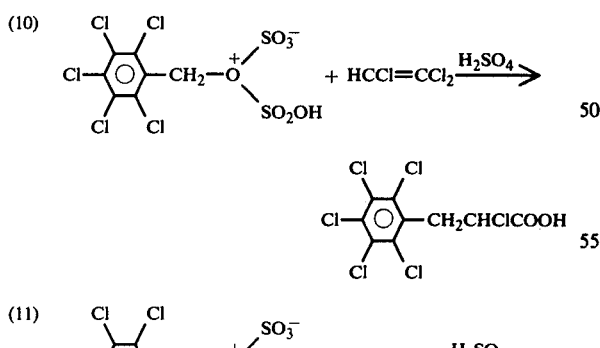
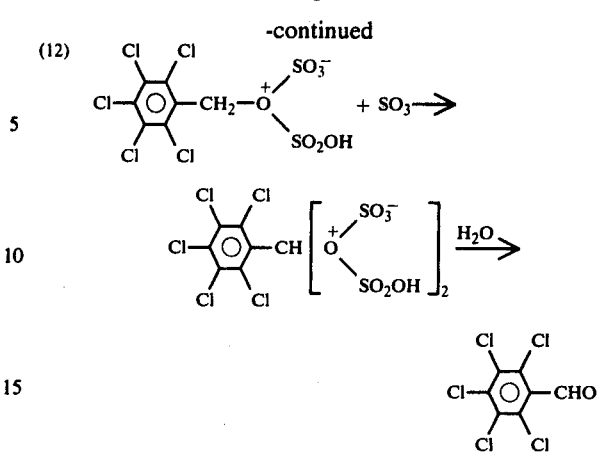

A variant of these reactions was encountered with haloaromatic compounds which carry more than one methyl group. When these reactants were oxidized with sulfur trioxide and the resultant oxonium compounds were decomposed by water, the reaction products were the corresponding di- or polyhydroxymethyl compounds analogous to the products of equation (1) When the oxidation was effected with a sulfur trioxide sulfuric acid mixture (as, for example, with 20% oleum) the reaction products were aldehydes in which one of the methyl groups remained intact. This unusual reaction (detailed in Examples 64–67) can be represented by equation (13) using tetrachloro-p-xylene as the specific reactant.

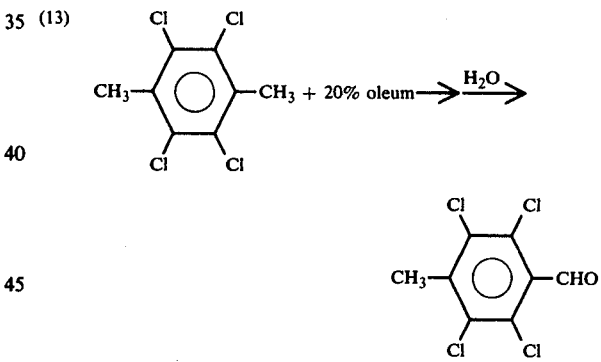

For contrast, when sulfur trioxide was used in the absence of sulfuric acid, the reaction followed the course depicted in equation (1a).

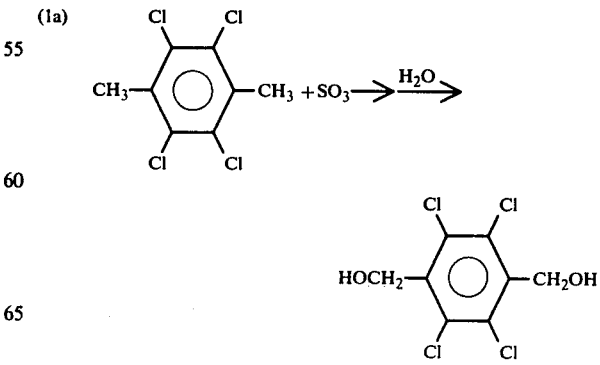

Even more surprisingly, when the diol itself was exposed to oleum, the methyl-aldehyde was the reaction product.

(14)
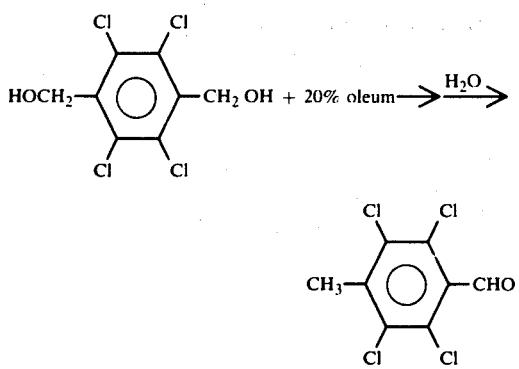

The products of these novel reactions can thus be categorized by the following generic formulae:

The products of reaction (1) can be represented by (B)

$$Hal_mAr(CH_2OH)_n \quad (B)$$

where Ar, Hal, M and n are the same as defined in generic formula (A).

The products of reaction (2) can be represented by (C)

$$Hal_mAr(CH_2OSO_2OM)_n \quad (C)$$

where Ar, Hal, m and n are as defined above and M is a metal comprising the alkali, the alkaline earth and other readily available cationic species.

The products of reactions (3), (4) and (5) can be represented by (D).

$$Hal_mAr(CH_2Hal')_n \quad (D)$$

where Ar, Hal, m and n are as defined above and Hal' is a halogen comprising chlorine, bromine and iodine.

The products of reaction (6) are represented by (E).

$$Hal_mAr(CH_2Ar)_n \quad (E)$$

where Ar, Hal, m and n are as defined above. Although illustrated only with benzene, suitable reactants include a wide range of aromatic compounds which contain at least one hydrogen available for the substitution reaction illustrated in (6). Thus suitable aromatic substrates include mono-, di- and polyhalobenzenes, such as fluorobenzene, chlorobenzene, o-dichlorobenzene, p-dichlorobromobenzene, 1,2,4-trichlorobenzene, bromobenzene, p-chlorobromobenzene, iodobenzene; mono-, di- and polyalkylbenzenes, such as toluene, xylenes, mesitylene, pseudocumene, durene, ethylbenzene, isopropylbenzene, tert-butylbenzene, o-chlorotoluene, dodecylbenzene; isolated and fused di- and polycyclic aromatic compounds, such as biphenyl, naphthalene, anthracene, phenanthrene, pyrene, 1-chloronaphthalene, 9,10-dichloroanthracene, triphenylmethane and indene.

The products of reactions (7) and (8) are shown by (F).

$$Hal_mAr(CH_2NHCR)_n \atop \|\;\;\;\;\;\;\;\;\;\;\;\;\;\;\;\;\;\;\;\;\;\;\;\;O \quad (F)$$

where Ar, Hal, m and n are as defined above and R is a hydrocarbon residue comprising aliphatic, cyclo-aliphatic and aromatic groups which may be substituted by halogens.

Suitable reactants for reactions (7) and (8) thus include hydrogen cyanide, acetonitrile, propionitrile, butyronitrile, trichloracetonitrile, trifluoroacetonitrile, benzonitrile, p-chlorobenzonitrile, acrylonitrile, propiolic acid nitrile, as well as di- and polynitriles, such as cyanogen, glutaronitrile, adiponitrile, phthalonitrile. When di- or polyfunctional oxonium compounds, such as those derived from xylene and mesitylene are reacted with difunctional nitriles, such as malononitrile, succinonitrile, adiponitrile, polymeric polyamides are produced.

The products of reaction (9) are represented by (G):

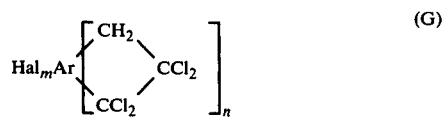

where Ar, Hal, m and n are as defined above. The products of reaction (10) are represented by (H):

$$Hal_mAr(CH_2CHClCOOH)_n \quad (H)$$

where Ar, Hal, m and n are as defined above

The products of reaction (II) are shown by (I):

$$Hal_mAr(CH_2CCl_2COOH)_n \quad (I)$$

where Hal, Ar, m and n are as defined above.

The product of reaction (12) are represented by (J):

$$Hal_mAr(CHO)_n \quad (J)$$

where Hal, Ar, m and n are as defined above.

The products of reactions (13) and (14) are represented by (K):

$$Hal_mAr(CH_3)_p(CHO)_q \quad (K)$$

where Ar, Hal, m are as defined above, and p and q are integers with the following relationship: $p = q = n$, where n is the same as defined above.

These reactions which are characterized by high conversion and by the purity of the products and which take place in analogous fashion with various mono-, di-, and tri-oxonium compounds as well as other halogenated aromatic compounds are thus eminently suitable for preparative (manufacturing) processes. The variety of mono-, di- and polyfunctional end products of these reactions find uses as additives or polymers which they render fire resistant by virtue of their high halogen content, as monomers for the preparation of a variety of polymeric systems, as chemical intermediates and as pesticides.

The following examples are given for purposes of illustration of this invention and are not to be construed as limiting it except as set forth in the claims.

EXAMPLE 1

Preparation of 2,3,4,5,6-pentachlorobenzyldisulfooxonium hydroxide inner salt from pentachlorotoluene and sulfur trioxide

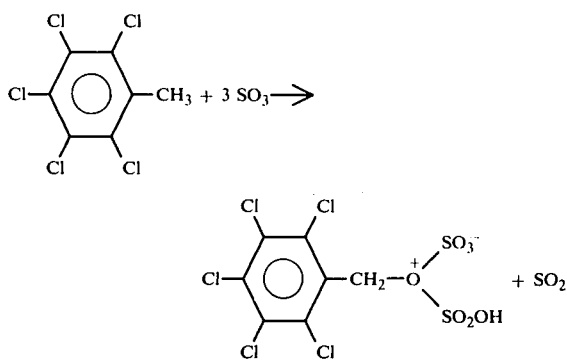

Liquid sulfur trioxide, (200 ml, 385 g) was added to 26.4 g. (0.1 mole) of pure 2,3,4,5,6-pentachlorotoluene (mp 224°-225° C.) placed in a 500 ml 3-neck tared flask provided with stirrer, thermometer and reflux condenser the end of which was attached to a bubble counter so that the rate of gas evolution during the reaction can be visually estimated. External heat was applied to the flask to bring the sulfur trioxide to reflux. Soon a light blue color developed, which turned gradually deeper to a vivid royal blue. The color change was accompanied by gas evolution which was identified as sulfur dioxide. The steady gas evolution, which began after 10 minutes of reflux, lasted for 2-3 hours, after which it became gradually slower and the reaction mixture gradually acquired a dark green-gray color. The weight of the reaction mixture at this time indicated a loss of 6.9 g, as compared to the theoretical loss of 6.4 g, corresponding to one mole of sulfur dioxide evolved. The excess of sulfur trioxide, which acted also as a solvent during the reaction was distilled off first at atmospheric pressure, then under aspirator vacuum at a temperature not exceeding 70° C. The weight (45.2 g) of the product, a greenish-grey solid, indicated as $C_7H_3Cl_5O_7S_2$ composition and this was confirmed by its hydrolysis which yielded 0.2 moles of sulfuric acid and 0.1 mole of pentachlorobenzyl alcohol, identified by elemental analysis, infrared spectroscopy, melting point and nuclear magnetic resonance spectroscopy (see Example 23). The evolvement of the reaction was also followed by nuclear magnetic resonance (nmr) spectroscopy which indicated that even in the early stages of the reaction the characteristic proton resonance of pentachlorotoluene at 2.52 ppm downfield from tetramethylsilane (TMS) completely disappeared. Instead, a new peak at 4.55 ppm appeared, which is assignable to the radical cation formed from pentachlorotoluene by the loss of one electron. During the refluxing and sulfur dioxide eveolution period two additional peaks developed in increasing intensities and in approximately in a 2:1 ratio at 6.29 and 9.21-9.60 ppm (the later is somewhat variable during the reaction). The former corresponds to the two benzylic hydrogens adjacent to the oxonium moiety and the latter corresponds to the acidic proton of the sulfuric acid moiety. The intensity of the peak corresponding to the radical cation, which accounts for the intense blue color, diminishes to a few percent after 2 hours of reflux and the intensities of the protons of oxonium compound become constant after this period.

EXAMPLE 2

Preparation of pentachlorobenzyldisulfooxonium hydroxide inner salt from pentachlorobenzyl alcohol and sulfur trioxide

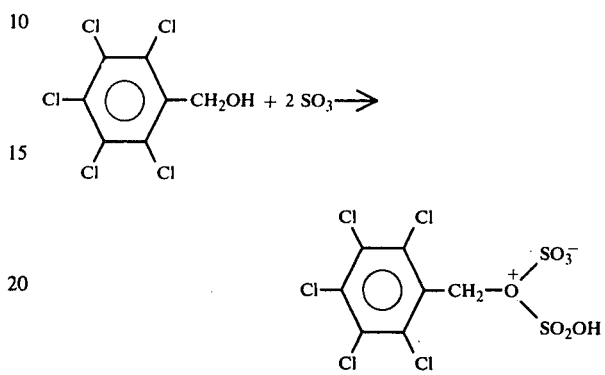

The procedure of Example 1 was repeated, except that the equivalent amount (28.0 g) of pentachlorobenzyl alcohol, mp 195°-196° C. was substituted for pentachlorotoluene. In contrast to the former case only a transient blue color appeared which on reflux turned greyish green, but there was no gas evolution. The identity of the product was that of the former example was established by nuclear magnetic resonance, which showed the two peaks of the oxonium compound.

EXAMPLE 3

Preparation of pentachlorobenzyl(chlorosulfonyl)sulfooxonium hydroxide inner salt for pentachlorobenzyl chloride and sulfur trioxide

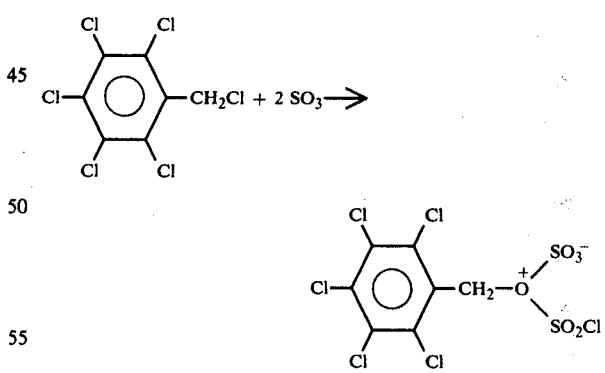

The procedure of Example 1 was repeated, except that the equivalent amount (29.9 g) of pentachlorobenzyl chloride, mp 100°-101° C., was substituted for pentachlorotoluene. A 10 minute refluxing period sufficed to convert the halide into the halooxonium compound, without gas evolution and without the occurrence of a highly colored solution. For subsequent reaction of this product see Examples 49 and 58. The chemical shift of this oxonium compound was at 6.35 ppm in $SO_3$ solution.

EXAMPLE 4

Preparation of the monooxonium compound from pentabromotoluene and sulfur trioxide

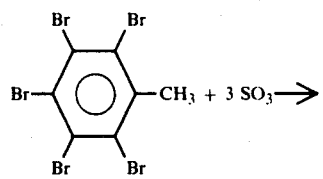

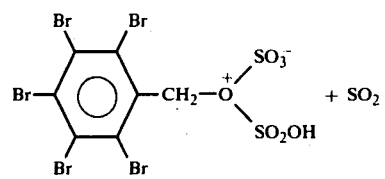

When the procedure of Example 1 was repeated with the substitution of 48.7 g 2,3,4,5,6-pentabromotoluene (mp 284°–286° C.) for pentachlorotoluene, gas evolution and the development of a dark green color accompanied the formation of the oxonium compound which was obtained in quantitative yield.

EXAMPLE 5

Preparation of the monooxonium compound from pentafluorotoluene and sulfur trioxide

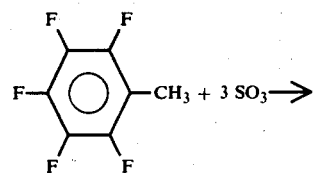

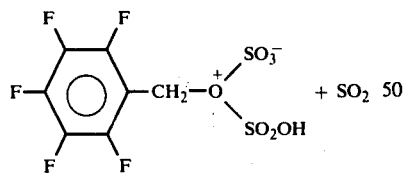

The procedure of Example 1 was repeated except that 18.2 g of 2,3,4,5,6-pentafluorotoluene bp 117°–118° C., $n_D^{20}$ 1.4023, was substituted for pentachlorotoluene and that the refluxing period was extended to six hours. The originally colorless solution after 3 hours turned deep red and the methyl protons at 2.44 ppm disappeared, giving rise to the methylene protons at 6.05 ppm and the acid proton at 9.58 ppm. The oxonium compound was hydrolyzed to the benzylic alcohol as described in Example 68.

EXAMPLE 6

Preparation of pentachlorobenzalbis(disulfooxonium)dihydroxide bis(inner salt) from pentachlorotoluene and sulfur trioxide

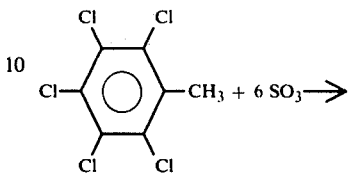

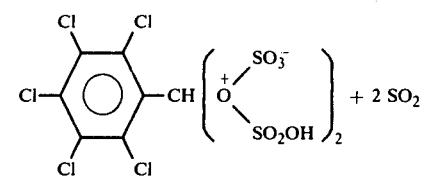

The procedure of Example 1 was repeated, except that the refluxing period of sulfur trioxide was extended to 24 hours. At the end of this period the reaction product weighed 398.2 g, thus indicating a weight loss of 13.2 g, corresponding to the evolution of 0.2 moles of sulfur dioxide. Distillation of the excess of sulfur trioxide resulted in the recovery of 313 g. of material, or 93% of the theory. Stripping of the reaction mixture under the vacuum of a water aspirator resulted in a further weight loss of 22 g., and the isolation of 61.1 g. of the dioxonium compound, which represents an essentially quantitative yield.

The identification of the dioxonium compound was done by nuclear magnetic resonance which showed two peaks at 8.9 and at 10.15 ppm, and by the quantitative analysis of its hydrolysis products, which included four mole equivalents of sulfuric acid and one mole equivalent of pentachlorobenzaldehyde (see Example 33). The formation of sulfur dioxide and of the solid product in quantitative yields is ompatible only with the stoichiometry indicated above.

EXAMPLE 7

Preparation of the dioxonium compound from pentabromotoluene and sulfur trioxide

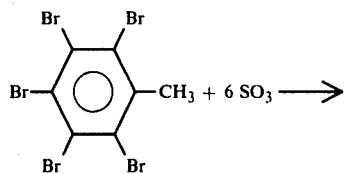

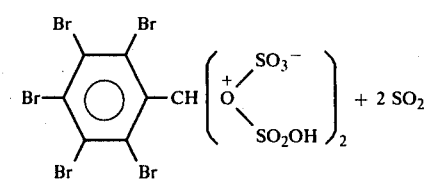

The procedure of Example 6 was repeated, except that 48.7 g. of 2,3,4,5,6-pentabromotoluene (mp. 284°–286° C.) was substituted for pentachlorotoluene. The dioxonium compound was identified by the elemental analysis of its hydrolysis products, which included four moles of sulfuric acid and one mole of pentabromobenzaldehyde (see Example 35), as well as by its formation in quantitative yield by the stoichiometry shown above.

EXAMPLE 8

Preparation of pentachlorobenzal (chlorosulfonyl)sulfooxonium hydroxide (disulfooxonium hydroxide)bis(inner salt) from pentachlorobenzyl chloride and sulfur trioxide

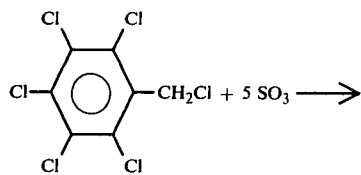

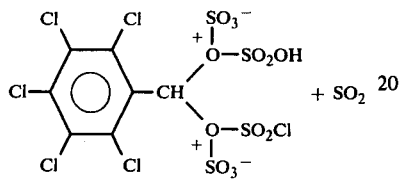

The procedure of Example 3 was repeated, except that the heating period was extended to 24 hours. Stripping of the excess of sulfur trioxide and hydrolysis of the dioxonium compound resulted in the formation of four moles of sulfuric acid, one mole of hydrochloric acid and one mole of pentachlorobenzaldehyde, mp. 201°–203° C.

EXAMPLE 9

Preparation of 2,3,4,5-tetrachloro(p-phenylenedimethylene)-bis(disulfooxonium dihydroxide)bis(inner salt) from 2,3,5,6-tetrachloro-p-xylene and sulfur trioxide

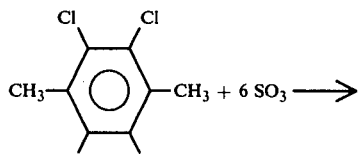

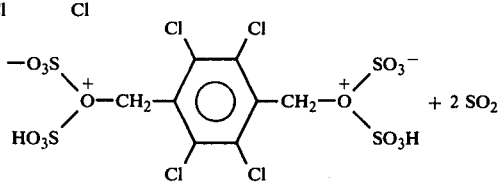

The procedure of Example 1 was repeated, except that 24.4 g. of 2,3,5,6-tetrachloro-p-xylene, mp. 218°–219° C. was substituted for pentachlorotoluene. The oxidation step of the xylene was apparently faster than that of the toluene as judged by the vigor of the sulfur dioxide evolution on refluxing the purple solution of the radical cation. After a refluxing period of 0.5 hour only 5% radical cation was left in solution, which contained 95% of the dioxonium compound, characterized by the proton nuclear magnetic resonance peaks at 6.36 and 9.73 ppm in the correct 2:1 ratio. Distillation of the excess of sulfur trioxide resulted in a 93% efficiency in its recovery and the isolation of the dioxonium compound in 93% yield. In addition to the nuclear magnetic resonance data given above the new product was characterized also by the quantitative analysis of its hydrolysis products, which included four mole equivalents of sulfuric acid and one mole equivalent of tetrachloro-p-xylene diol as well as by its additional derivatives (see Examples 41 and 47).

EXAMPLE 10

Preparation of the dioxonium compound from 2,4,5,6-tetrachloro-m-xylene and sulfur trioxide

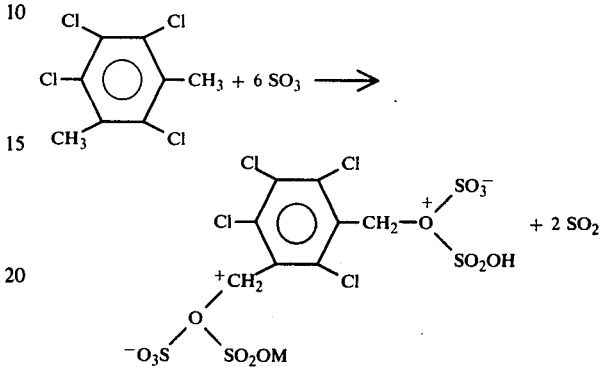

The procedure of Example 9 was repeated, except that 2,4,5,6-tetrachloro-m-xylene, mp. 220°–222° C., eas substituted for the para isomer. The oxidation of the chlorocarbon occurred readily and was essentially complete after one hour of refluxing period, when the nuclear magnetic resonance of the purple solution indicated the absence of any starting material, the presence of only 2.5% of the radical cation (chemical shift at 4.68 ppm downfield from the references tetramethylsilane and the presence of the dioxonium compound in 97.5% abundance, as indicated by the chemical shifts at 6.40 and 9.83 ppm in the correct 2:1 ratio. Further identification of the novel compound was done by elemental and spectral analysis of its hydrolysis products, which include, after the stripping of the excess of sulfur trioxide, four moles of sulfuric acid and the formation of one mole equivalent of tetrachloro-m-xylene diol (see Examples 42 and 51).

EXAMPLE 11

Preparation of the dioxonium compound from 3,4,5,6-tetrachloro-o-xylene and sulfur trioxide

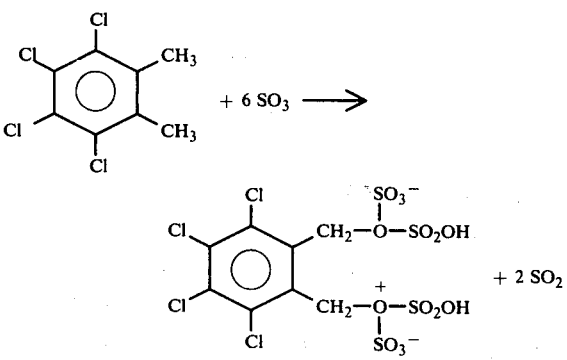

The procedure of Example 9 was repeated except that 3,4,5,6-tetrachloro-o-xylene, mp. 226°–228.5° C., was substituted for the para isomer. The formation of the radical cation and of the dioxonium compound occurred readily as evidenced by the immediate development of a deep purple solution and the copious evolution of sulfur dioxide on heating. Identification of the dioxonium compound was done as in the previous examples, except that on hydrolysis only three equivalent moles of sulfuric acid were produced, in addition to one mole equivalent of the cyclic sulfate of tetrachloro-o-xylene (see Example 31). The presence of the dioxonium compound, as shown in the title structure, was diagnosed directy by proton nuclear magnetic resonance, which identified the benzylic protons by a singlet at 6.32 ppm and the acidic protons at 9.99 ppm in the correct 2:1 ratio.

EXAMPLE 12

Preparation of the dioxonium compound from 2,3,5,6-tetrabromo-p-xylene and sulfur trioxide

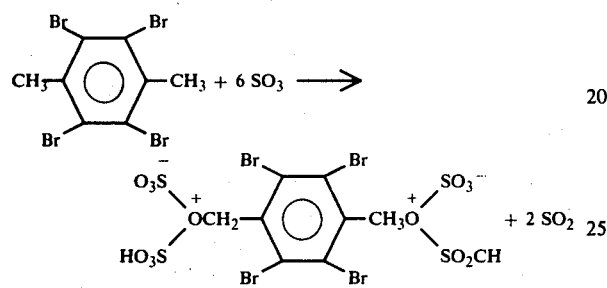

The procedure of Example 9 was repeated except that 42.2 g of 2,3,5,6-tetrabromo-p-xylene, mp 251.5°–252.8° C., was substituted for the corresponding tetrachloro compound. The oxidation of the chlorocarbon occurred readily as evidenced by the formation of a deep blue-green slurry, indicative of the radical species, and by the evolution of sulfur dioxide. Proton nuclear magnetic resonance of the sulfur trioxide solution showed even only after one hour of reaction time, the absence of starting material (by the absence of the methyl protons at 2.79 ppm) and the presence in 98% of the dioxonium compound by the presence of the benzylic protons at 6.66 ppm and of the acidic protons at 9.96 ppm in the correct 2:1 ratio, and the presence of only 2% of the radical species by a peak at 4.74 ppm. Hydrolysis of the highly reactive dioxonium compound, a dark, solid product yielded four mole equivalents of sulfuric acid, as evidenced by titration, and one mole equivalent of 2,3,5,6-tetrabromo-p-xylene-1,4-diol (see Example 29 as well as Examples 44 and 45).

EXAMPLE 13

Preparation of the dioxonium compound from 2,4,5,6,-tetrabromo-m-xlene and sulfur trioxide

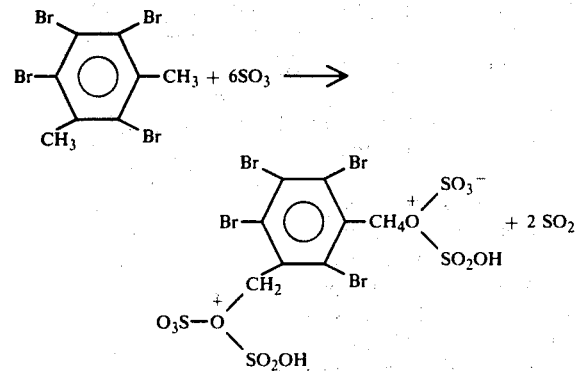

The procedure of Example 12 when applied to 2,4,5,6-tetrabromo-m-xylene, mp 251°–252° C., yielded the corresponding dioxonium compound, as evidenced by its isolation as a reactive solid material in quantitative yield as well as by its hydrolysis, again in quantitative yield, to four mole equivalents of sulfuric acid and one mole equivalent of 2,4,5,6-tetrabromo-m-xylene-1,3-diol (see Experiment 30).

EXAMPLE 14

Preparation of the dioxonium compound from 2,3,5,6-tetraiodo-p-xylene and sulfur trioxide

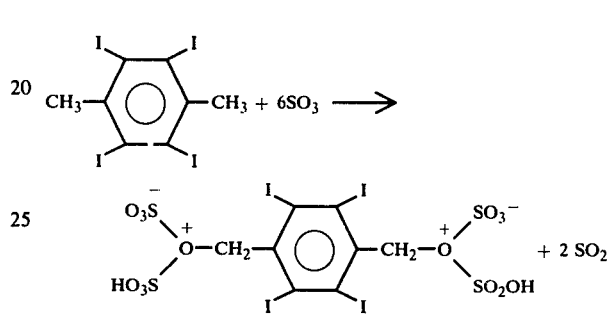

Repeating the procedure of Example 9 with 61.0 g of 2,3,5,6-tetraiodo-p-xylene, mp 245°–247° C., in place of the tetrachloro analog resulted in the facile oxidation of the iodocarbon and the formation of the dioxonium compound in quantitative yield.

EXAMPLE 15

Preparation of the dioxonium compound from 1,3,5,7-tetrabromo-2,6-dimethylnaphthalene and sulfur trioxide

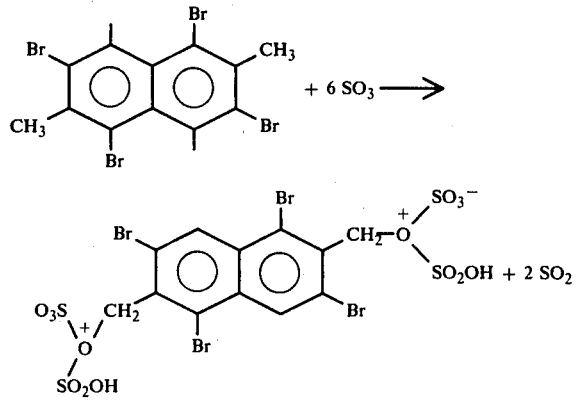

When the procedure described in Example 12 was repeated with the replacement of the tetrabromoxylene with 47.2 g. of 1,3,5,7-tetrabromo-2,6-dimethylnaphthalene, mp 226°–229° C., the formation of the dioxonium compound occurred readiy in the fashion described in the previous examples.

EXAMPLE 16

Preparation of 2,4,6-tribromo-s-pheneyltris(methylene)-tris[disulfooxonium]trihydroxide tris (inner salt) from 2,4,6-tribromomestitylene and sulfur trioxide

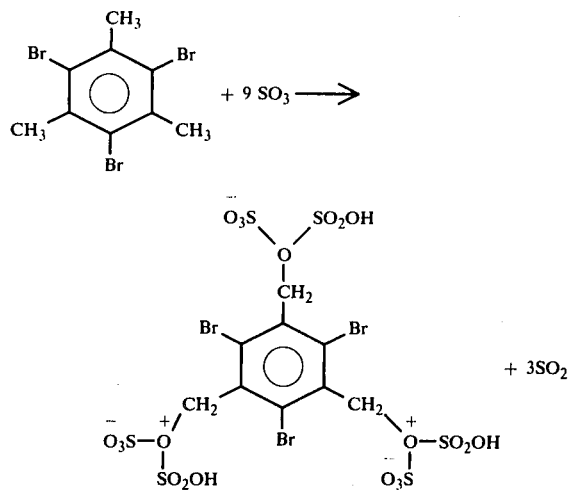

The procedure described in Example 12 was repeated, except that the tetrabromo-p-xylene was replaced with 35.7 g of 2,4,6-tri-bromomesitylene, mp 215°–217° C. A very facile oxidation of the bromocarbon occurred with copious evolution of sulfur dioxides, resulting in the formation of the trioxonium compound in quantitative yield.

EXAMPLE 17

Preparation of the dioxonium compound from 2,3,5,6-tetrachloro-p-xylene-1,4-diol and sulfur trioxide

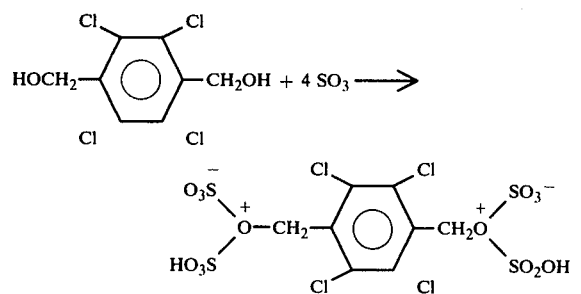

The dissolution of 27.6 g of 2,3,5,6-tetrachloro-p-xylene-1,4-diol in 100 ml (197 g) of liquid sulfur trioxide took place without the evolution of sulfur dioxide, which did not commence even after 3 hours of refluxing. Stripping of the excess of sulfur trioxide resulted in the isolation of the dioxonium compound identical with the one obtained in Example 9.

EXAMPLE 18

Preparation of 2,3,5,6-tetrachloro (p-phenylenedimethylene)bis[(chlorosulfonyl)sulfooxonium]dihydroxide bis(inner salt from α,α',2,3,5,6-hexachloro-p-xylene and sulfur trioxide

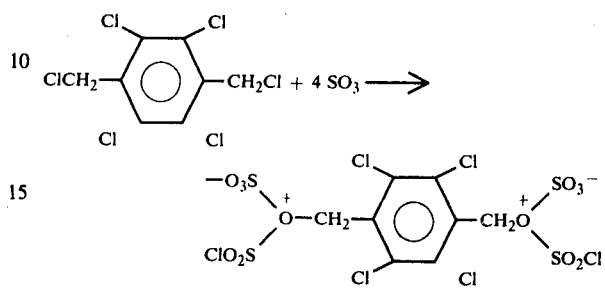

The procedure of Example 3 was repeated except that 31.3 g of a α,α',2,3,5,6-hexachloro-p-xylene, mp 179°–181° C., was substituted for pentachlorobenzyl chloride. Although a deep purple solution was formed, no evolution of sulfur dioxide occurred. The deep purple component of the reaction mixture was identified as the benzylic radical by its nuclear magnetic resonance peak at 4.69 ppm whereas the dioxonium compound was also identified by its chemical shift at 6.41 ppm, as well as by its hydrolysis in quantitative yield to four equivalent moles of sulfuric acid, two equivalent moles of hydrochloric acid and one equivalent mole of 2,3,5,6-tetrachloro-p-xylene-1,4-diol (see Example 69).

EXAMPLE 19

Preparation of the dioxonium compound from α,α',3,4,5,6-hexachloro-o-xylene and sulfur trioxide

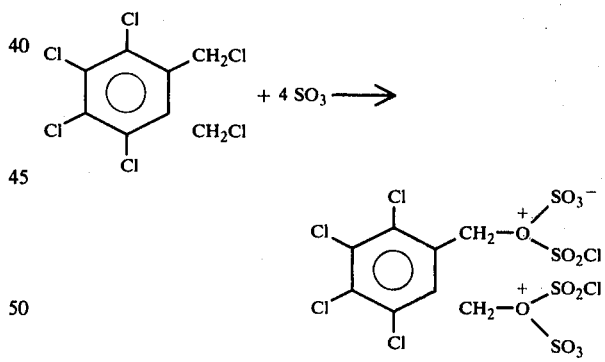

The procedure of Example 3, when applied to 31.3 g of α,α',3,4,5,6-hexachloro-o-xylene, mp 92°–92.5° C., yielded an intensely purple solution but essentially no sulfur dioxide evolution even during a refluxing period of 3 hours. The intermediate biradical was identified by its nuclear magnetic resonance peak at 4.65 ppm (present in about 8–10% abundance in the reaction mixture), whereas the dioxonium compound (90–92% of the reaction mixture) had the chemical shift of its protons at 6.31–6.33 ppm. After the stripping of the excess of sulfur trioxide, the dioxonium compound was obtained as a dark amber colored viscous oil in quantitative yield (63.5 g) and was further identified by its hydrolysis to three mole equivalents of sulfuric acid, two mole equivalents of hydrochloric acid and one mole equivalent of the cyclic sulfate of 3,4,5,6-tetrachloro-o-xylene-1,2-diol (see Example 32).

EXAMPLE 20

Preparation of a transient oxonium compound from 2,3,4,5,6-pentachloroethylbenzene and sulfur trioxide

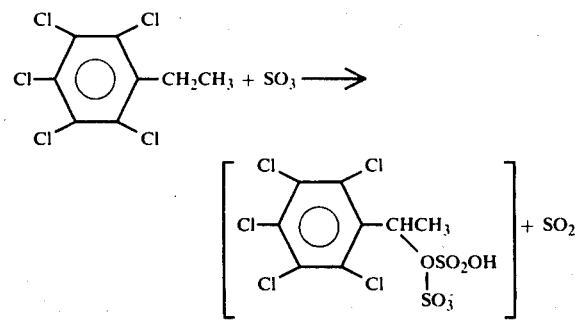

The procedure of Example 1 was repeated, except that 27.8 g (0.1 mole) of 2,3,4,5,6-pentachloroethylbenzene, mp 56°–57° C., was substituted for pentachlorotoluene. Oxidation of the chlorocarbon was evidenced by the formation of the colored (deep purple) radical cation, by the evolution of sulfur dioxide as well as by hydrolysis experiment (see Example 62).

Although the transient oxonium product of this experiment was not isolated, its structure may be infered by consideration of the reactants and the product of Example 62, infra. Likewise, the material balance based upon $SO_2$ evolution evidenced the formation of the oxonium salt depicted supra.

The following examples illustrate the usefulness of the oxonium compounds for the preparation of a large variety of novel as well as known halogen containing compounds in simple reactions and in high conversions.

EXAMPLE 21

Preparation of the sodium salt of pentachlorobenzyl hydrogen sulfate

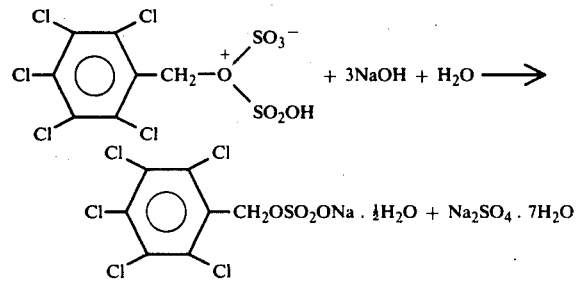

The oxonium salt prepared in Example 1 was added gradually and with cooling to 1 liter of 75:25 (vol/vol) mixture of water and ethyl alcohol. After filtration to the resultant solution there was added 200 ml of a 1.0 normal aqueous sodium hydroxide solution, whereby a white crystalline salt separated out of the solution and was identified as the title compound by elemental analysis and nuclear magnetic resonance.

Calculated for $C_7H_2Cl_5NaO_4S \cdot \frac{1}{2}H_2O$: C, 21.5; H, 0.77; Cl, 45.3; S, 8.2%; Found: C, 21.6; H, 0.8; Cl, 43.2; S, 8.5%.

Nuclear magnetic resonance in dimethyl sulfoxide (DMSO) showed a singlet methylene at 5.05 ppm (area 2) and a water peak at 3.30 ppm (area 1.).

EXAMPLE 22

Preparation of the ammonium salt of pentachlorobenzyl hydrogen sulfate

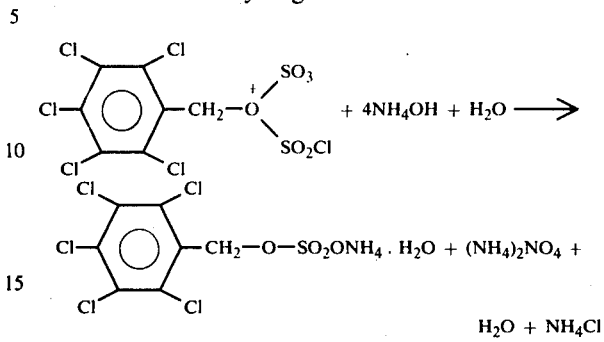

The procedure of Example 21 was repeated, except that the reaction product obtained in Example 3 was added to a concentrated solution of aqueous ammonium hydroxide The title compound, which crystallized out, was isolated by filtration in 42% conversion and was identified by elemental analysis and by its proton nuclear magnetic resonance spectrum.

Calculated for $C_7H_6Cl_5NO_4S \cdot \frac{1}{2}H_2O$: C, 21.3; H, 1.8; Cl, 44.2; N, 3.7; S, 8.9%. Found: C, 21.7; H, 1.8; Cl, 45.8; N, 3.6; S, 8.8%.

Nuclear magnetic resonance (in DMSO) showed a singlet methylene at 5.09 ppm and a broad band at 7.1–7.4 ppm corresponding to the protons of the ammonium cation.

EXAMPLE 23

Preparation of 2,3,4,5,6-pentachlorobenzyl alcohol

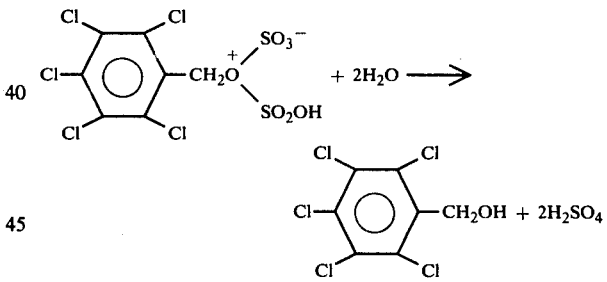

The light greenish, solid residue obtained by repeating the procedure of Example 1, was added to 500 ml of water, followed by heating the resultant white aqueous slurry to reflux for 15 minutes. Filtration yielded a white, powdery material, which after filtration, washing and drying weighed 26.6 g. Its purification was effected by refluxing it with 150 ml of glacial acetic acid, containing a trace of sulfuric acid, for a period of 20 minutes, followed by filtration of a small amount (2.7 g) of insoluble material, identified below. Excess of acetic acid was distilled off from the filtrate and the resultant solid residue was refluxed for 30 minutes with 200 ml of 10% methanolic potassium hydroxide solution. The resultant reaction mixture was poured into water and the solid precipitate was filtered. Washing with water and subsequent dryings yielded 24.5 g of pure 2,3,4,5,6-pentachlorobenzyl alcohol, mp 195.0°–196.5° C., which corresponds to 91% yield. Confirmation of its structure was done by comparison of its infra-red and nuclear magnetic resonance spectral properties with those of an authentic specimen, as well as by mixed melting point. A dilute DMSO solution of the experimental sample showed a doublet at 4.74 ppm, corresponding to the benzylic protons and a triplet at 5.50 ppm (at 34° C.; and 5.39 ppm at 60° C.) corresponding to the hydroxylic proton. The multiplicity is caused by mutual coupling with a J value of circa 5.5 cps. The two multiplets were present in the correct 2:1 ratio of the corresponding areas.

The 2.7 g of material found insoluble in acetic acid was separated by trituration with hot toluene into a soluble fraction and an insoluble fraction. The hot toluene solution on cooling yielded 1.75 g of a white crystalline material, identified as decachlorodibenzyl ether, mp 223°–225° C., by infra-red, nuclear magnetic resonance, and mixed melting point of an authentic specimen. Its infra-red spectrum, determined in tetrachloroethylene and carbon disulfide solutions, had strong maxima at 1365, 1232, 1125, 1078 and 682 cm$^{-1}$. Its proton nuclear magnetic resonance spectrum displayed a singlet at 4.92 ppm, as determined in deuteriochloroform solution.

The 0.5 g of the hot toluene insoluble material was identified by infra-red, nuclear magnetic resonance and mass spectroscopy as a mixture of 2,3,4,5,6,2',3',4',5',6'-decachlorodiphenylmethane (0.25 g), 2,4,5,6,2',3',4',5',6'-nonochloro-3-methyldiphenylmethane (0.12 g) and 2,3,5,6,2',3',4',5',6'-nonachloro-4-methyldiphenylmethane (0.13 g).

Similar, almost identical, results to these were obtained also when the residues of Experiments 2 and 3 were worked up by the procedure outlined in Example 23.

EXAMPLE 24

Preparation of the disodium salt of 2,3,5,6-tetrachloro-p-xylene-α,α'-diol dihydrogen sulfate

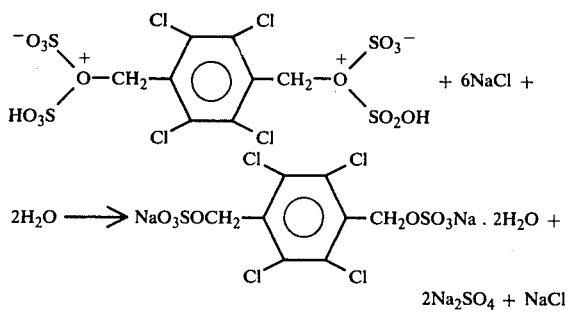

When the dark residue obtained after the stripping of unreacted sulfur trioxide in Example 9 was added to a mixture of ice and saturated sodium chloride solution, a white solid was formed, which after filtration and air drying weighed 24.1 g. Recrystallization from water gave an analytically pure sample of the title compound with a characteristic proton nuclear magnetic resonance singlet of the benzylic protons at 5.13 ppm and the water protons at 3.40 ppm, in DMSO solution.

Calculated for $C_8H_4Cl_4Na_2O_8S_2.2H_2O$: C, 18.64; H, 1.56; Cl, 27.41; $H_2O$, 7.01%. Found: C, 19.0; H, 1.4; Cl, 28.7; $H_2O$, 7.3%.

EXAMPLE 25

Preparation of 2,3,5,6-tetrachloro-p-xylene-α,α'-diol

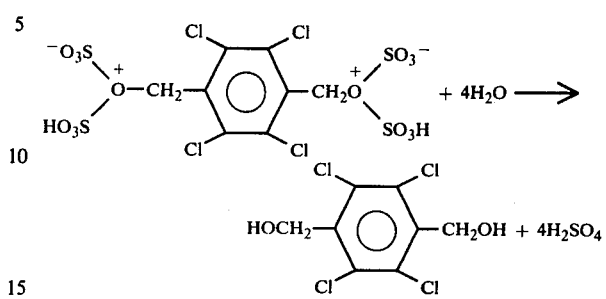

When the dioxonium compound obtained in Example 9 was added to ice and the resultant white slurry was refluxed with an equal amount of 20% aqueous hydrochloric acid solution, a readily filtrable white precipitate was obtained, which was washed with water and dried. Recrystallization from dioxane yielded white crystals, mp 226°–230°, found to be identical by mixed melting point, infra-red and nuclear magnetic resonance with authentic 2,3,5,6-tetrachloro-p-xylene-α,α'-diol.

The infra-red spectrum of the pure diol, ran in FLUOROLUBE and mineral oil mull had maxima at 3200, 1350, 1240, 1185, 1130, 1035, 1018, 950, 828, 690, 650 and 525 cm$^{-1}$. The nuclear magnetic resonance spectrum of a DMSO solution displayed the methylene protons as a doublet at 4.67 ppm and the hydroxylic proton at 5.32 ppm as a triplet.

An alternate workup of the residue of Experiment 9 yields the diol directly. It consists of adding the dark residue to ice and heating the resultant slurry on the steam bath until the hydrolysis of the hydrogen sulfate ester is essentially complete. Filtration of the slightly off-white precipitate and washing it with water results, even without recrystallization, in a nearly quantitative yield of the pure diol.

EXAMPLE 26

Preparation of the disodium salt of 2,4,5,6-tetrachloro-m-xylene-α,α'-diol dihydrogen sulfate

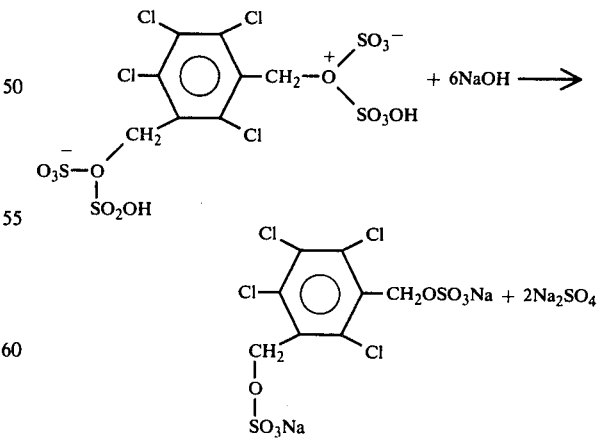

When the dark, almost black, residue of Experiment 10 was added to ice and neutralized with 400 ml of ice cold 10% sodium hydroxide solution, a clear solution of the sodium salt of the sulfuric acid ester resulted. Evaporation of all of the free water yielded 104.8 g of a slightly pinkish solid, the proton nuclear magnetic resonance spectrum of which, in DMSO solution, indicated it to be predominatly the title compound by the presence of the benzylic protons at 5.07 ppm (the reaction mixture, obtained after the stripping of water, contains, as indicated by the stoichiometry, also 2 mole equivalents of hydrated sodium sulfate). Elution with hot methanol (1000 ml) left behind much of the inorganic salt, but the isolation of an analytically pure organic sample was not achieved, due to the high solubility of this compound in water.

EXAMPLE 27

Preparation of 2,4,5,6-tetrachloro-m-xylene-α,α'-diol

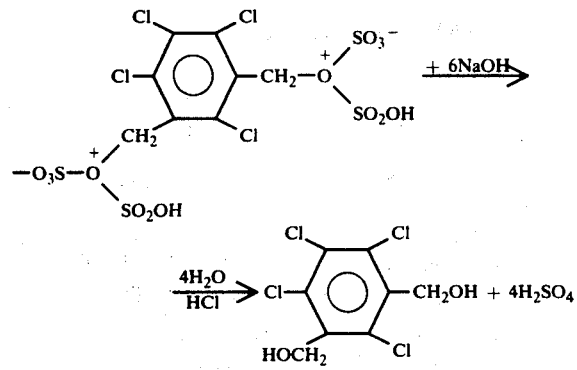

The process of Example 26 was repeated and the solid product (104.8 g) was dissolved in 325 ml of water and acidified with 110 ml of concentrated hydrochloric acid, evaporation of the volatile inorganic materials left behind 132 g of residue, which after water wash, filtration and drying yielded 22.3 g or 81% of pure 2,4,5,6-tetrachloro-m-xylene-α,α'-diol, mp 228°-230° C., whose identity was corroborated by its infra-red and nuclear magnetic resonance spectra, as well as by mixed melting point. Thus its infrared spectrum (run in Nujol mull) had maxima at 3250, 1430, 1350, 1310, 1265, 1250, 1110, 1015, 965, 895, 652, 542 and 475 cm$^{-1}$; the nuclear magnetic resonance spectrum ran in DMSO, contained the benzylic hydrogens as a doublet at 4.72 ppm and the hydroxylic protons as a triplet at 5.37 ppm.

EXAMPLE 28

Preparation of the disodium salt of 2,3,5,6-tetrabromo-p-xylene-α,α'-diol bis(hydrogen sulfate)

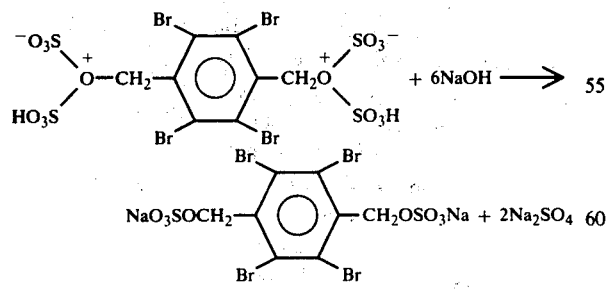

The dark solid residue obtained in Example 12 was added in small portions to ice water, parallel with the addition of an ice cold, 10% aqueous sodium hydroxide solution maintaining the pH slightly on the alkaline side. A total of 360 ml of the base was required. Filtration, followed by washing with ice water, yielded a filter cake, which after drying weighed 60.6 g or approximately 92% of the theoretical amount. Nuclear magnetic resonance spectroscopy confirmed its structure by the correct chemical shift of the benzylic protons at 5.23 ppm (DMSO solution).

EXAMPLE 29

Preparation of 2,3,5,6-tetrabromo-p-xylene-α,α'-diol

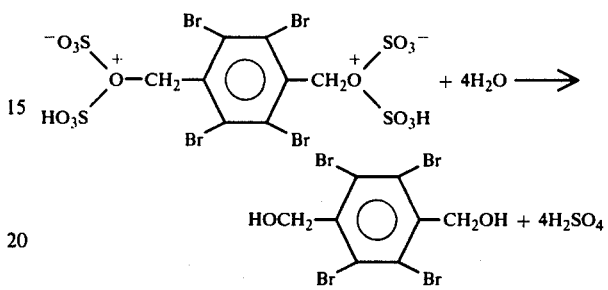

The solid residue of the stripping of sulfur trioxide in Example 12, was added to an excess (500 ml) of ice water, allowing the temperature to rise gradually. The resultant slurry was stirred mechanically and heated at reflux for one-half hour. Filtration and thorough washing of the filtercake yielded after drying, 41.2 g of a slightly off white product, which corresponds to 91% yield. Recrystallization from dioxane yielded off white crystals, mp 248°-252° C., whose infrared (maxima in Nugol mull at 3280, 1330, 1257, 1237, 1162, 1096, 1020, 983, 945, 812, 648, 575, 545 and 490 cm$^{-1}$) and nuclear magnetic resonance spectra (benzylic protons at 4.93 ppm; hydroxylic protons at 5.23 ppm in DMSO solution) confirmed its structure.

Calculated for $C_8H_6Br_4O_2$: C, 21.17; H, 1.33; Br, 70.44%. Found: C, 20.8; H, 0.9; Br, 70.0%

EXAMPLE 30

Preparation of 2,4,5,6-tetrabromo-m-xylene-α,α'-diol

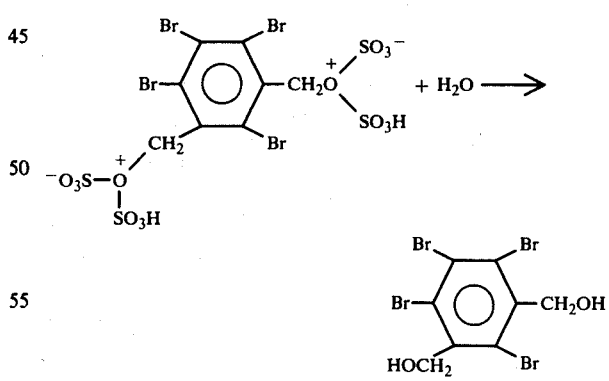

Repeating the procedure of Example 29 with the residue of Example 13 yielded the title compound in 93% yield; mp 248°-252° C. Infrared maxima in Nujol mull were at 3280, 1525, 1340, 1310; 1260, 1225, 1212, 1196, 1068, 1032, 1028, 996, 965, 952, 838, 625, 603 and 487 cm$^{-1}$, and nuclear magnetic resonance showed the benzylic protons at 4.95 ppm in DMSO solution.

Calculated for $C_8H_6Br_4O_2$: C, 21.17, H, 1.33; Br, 70.44%. Found: C, 21.0; H, 1.1; Br, 69.9%.

EXAMPLE 31

Preparation of the cyclic sulfate of
3,4,5,6-tetrachloro-o-xylene-α,α'-diol

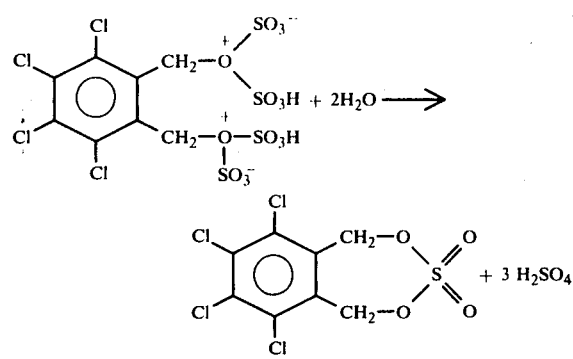

The dark pasty residue of Example 11 was added in portions to ice. The reaction was highly exothermic and yielded a rust colored product, which was filtered off, washed with water (or dilute aqueous sodium hydroxide) until it became free of acid. The product weighed 32.0 g or 95% of the theory. Recrystallization (twice) from trichloroethylene yielded yellow crystals, mp 186.0°–188.5° C., whose structure as the cyclic sulfate was confirmed by elemental analysis, molecular weight determination, infra-red and nuclear magnetic resonance spectroscopy.

Calculated for $C_8H_4Cl_4O_4S$: mol. wt, 338.01; C, 28.43; H, 1.19; Cl, 41.96; S, 9.49%. Found: mol. wt., 338 (by vapor phase osmometry, tetrahydrofuran solvent); C, 28.8; H, 1.2; Cl, 43.0; S, 9.8%.

Infrared maxima in $C_2Cl_4$ and $CS_2$ solutions occurred at 1420, 1380, 1330, 1308, 1278, 1212, 1198, 1176, 1031, 1004, 975, 950, 840, 658, 650, 645, 574, 566, 525, 514, 484 and 450 cm$^{-1}$.

Nuclear magnetic resonance (deuteriochloroform solution) displayed a singlet at 5.65 ppm, downfield from tetramethylsilane.

When worked up with neutralization by sodium hydroxide solution, the pasty solid of Example 11 occasionally yielded also smaller amounts of tetrachlorophthalan, mp. 214°–216° C. a known compound, identifiable readily in admixture with the cyclic sulfate, by the presence of a singlet at 5.12 ppm in its nuclear magnetic resonance spectrum, attributable to the benzylic protons.

EXAMPLE 32

Preparation of the cyclic sulfate of
3,4,5,6-tetrachloro-o-xylene-α,α'-diol

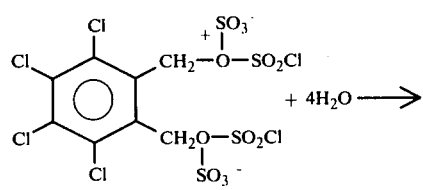

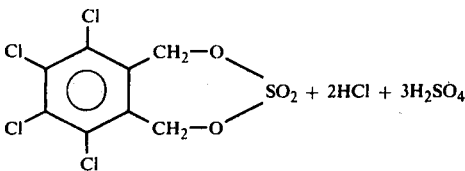

Addition of the distillation residue of Example 19 to ice or to ice cold dilute aqueous sodium hydroxide solution resulted in the formation of the cyclic sulfate described and identified in Example 31.

EXAMPLE 33

Preparation of pentachlorobenzaldehyde

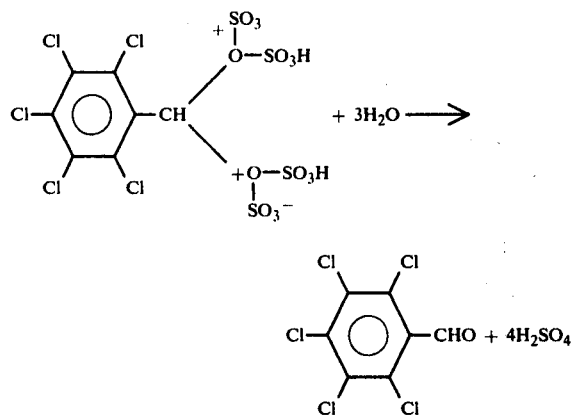

The addition of the dark dioxonium compound of Example 6 to 500 g of ice, followed by short heatings to 85° C. and filtration of the warm slurry, followed by water wash and drying resulted in the isolation of 26.6 g of a yellowish powdery material, shown to be pure pentachlorobenzaldehyde by gas chromatography, by nuclear magnetic resonance and infra-red spectroscopy. Recrystallization from chlorobenzene yielded pale yellow crystalline material, mp 201°–203° C., undepressed by the addition of authentic pentachlorobenzaldehyde. Its infrared spectrum, run in tetrachloroethylene and carbon disulfide solution, contained characteristic maxima at 2850, 1715, 1525, 1345, 1310, 1232, 1220, 1190, 1128, 946, 692, 659 and 522 cm$^{-1}$; its nuclear magnetic resonance spectrum displayed the aldehydic proton as a singlet at 10.32 ppm (deuteriochloroform solution) or at 10.26 ppm (in hexadeuteriodimethylsulfoxide).

EXAMPLE 34

Preparation of pentachlorobenzaldehyde

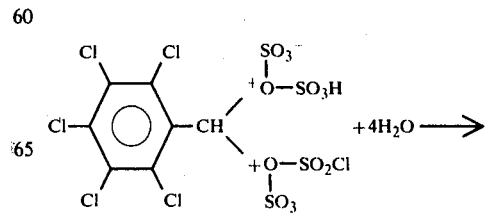

-continued

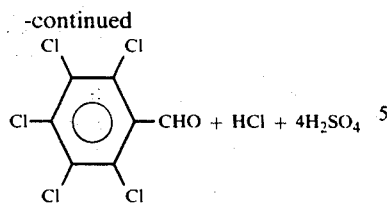
+ CHO + HCl + 4H$_2$SO$_4$

A workup similar to that of the preceding Example with the residue of Example 8 yielded again pentachlorobenzaldehyde, mp. 201°–203° in essentially quantitative conversion. The product was not contaminated by even traces of pentachlorobenzoic acid.

EXAMPLE 35

Preparation of pentabromobenzaldehyde

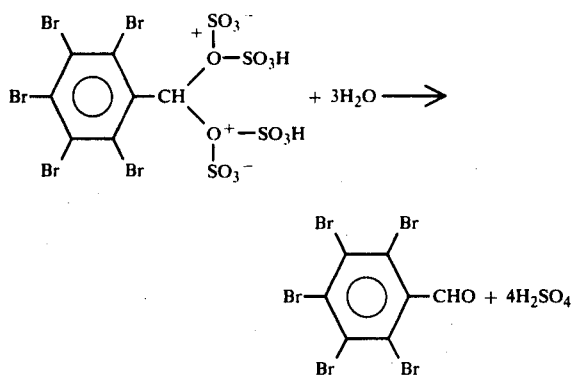

Addition of the dark residue of Example 7 to 500 g of ice, followed by short heating at 75°, filtration, washing and drying, resulted in the formation of 49.0 of a light brown powder, shown by gas chromatography to be 97.1% pure pentabromobenzaldehyde. The yield accordingly was 94.5%. Recrystallization from chlorobenzene improved the color and yielded the pure aldehyde in form of a light, cream colored, finely crystalline material, mp. 281°–283°, identified also by infra-red and nuclear magnetic resonance. Even the crude product was very pure and was free of pentabromobenzoic acid. Infrared analysis of the pure aldehyde in C$_2$Cl$_4$ and CS$_2$ solution showed maxima at 2840, 1720, 1300, 1250, 1170, 1068, 896 and 558 cm$^{-1}$; its nuclear magnetic resonance spectrum displayed the single proton at 9.81 ppm in DMSO and at 9.13 ppm in hexadeuteriobenzene solution.

EXAMPLE 36

Preparation of α,2,3,4,5,6-hexachlorotoluene

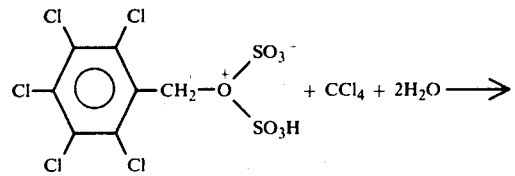
+ CCl$_4$ + 2H$_2$O ⟶

-continued

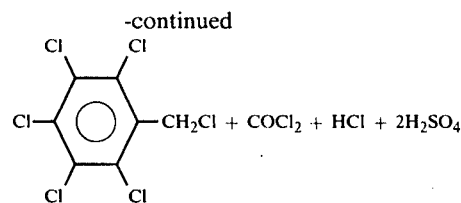
+ CH$_2$Cl + COCl$_2$ + HCl + 2H$_2$SO$_4$

The gradual addition with cooling of an excess (400 ml) of carbon tetrachloride to the oxonium compound prepared in Example 1 resulted in an exothermic reaction accompanied by strong gas evolution (phosgene and gaseous hydrochloric acid; good ventilation or, preferably, the absorption of the exit gases in strong aqueous alkali solution is recommended). After the addition was completed the resultant purplish solution was heated to reflux temperature (76°–80° C.) and kept there for twenty minutes. An additional amount of gas evolved during this period. Solid, anhydrous sodium carbonate was added to the reaction mixture in small portions until the evolution of carbon dioxide subsided. The resultant amber colored slush was filtered, rinsed with carbon tetrachloride, the solution was stripped of solvent on a rotating evaporator, yielding an amber liquid. This, added to ice, turned pale yellow and was filtered by suction and dried. Its structure as pentachlorobenzyl chloride (α,2,3,4,5,6-hexachlorotoluene) was established by its melting point (100°–101° C.) infrared and nuclear magnetic resonance, and its weight of 29.0 g indicated a 98% yield.

Infrared spectrum of the product, run in tetrachloroethylene and carbon disulfide solution, had maxima at 1355, 1302, 1272, 1240, 1128, 958, 926, 766, 698, 682, 608 and 495 cm$^{-1}$. Its nuclear magnetic resonance displayed the benzylic hydrogen as a singlet at 4.86 ppm, in deuteriochloroform solution.

EXAMPLE 37

Preparation of α,2,3,4,5,6-hexachlorotoluene

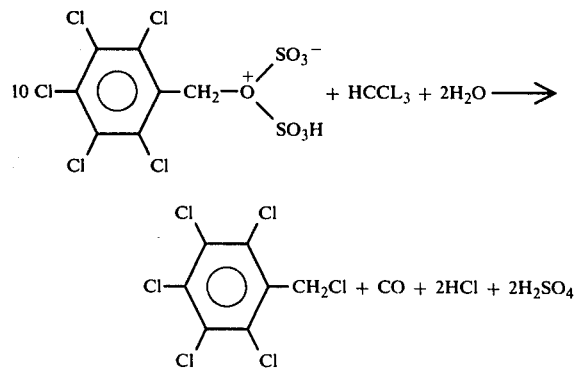

When chloroform was added, gradually and with external cooling to the solid residue of Example 1, followed by fifteen minutes refluxing and workup as described in Example 36, a high yield (circa 70 percent) of the title compound resulted.

EXAMPLE 38

Preparation of α,α,2,3,4,5,6-heptachlorotoluene

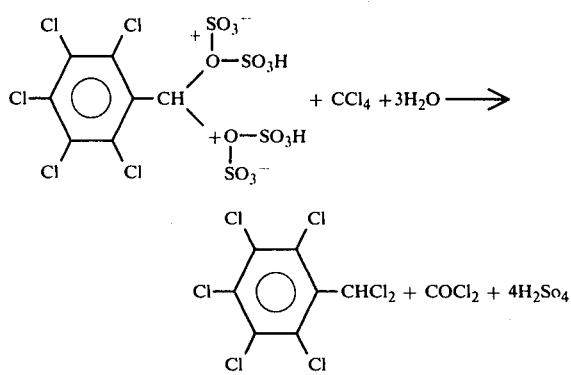

Repeating the procedure of Example 36 with the distillation residue of Example 6, instead of Example 1, resulted in the formation of α,α,2,3,4,5,6-heptachlorotoluene, (pentachlorobenzal chloride), mp. 118°–119° C. Its infrared spectrum, run in tetrachloroethylene and carbon disulfide solution, displayed maxima at 3045, 1540, 1352, 1278, 1232, 1227, 1127, 962, 776, 762, 712, 680, 614 and 506 cm$^{-1}$ and its nuclear magnetic resonance spectrum consisted of a single peak at 7.55 ppm in deuteriochloroform solution.

EXAMPLE 39

Preparation of α-bromo-2,3,4,5,6-pentachlorotoluene

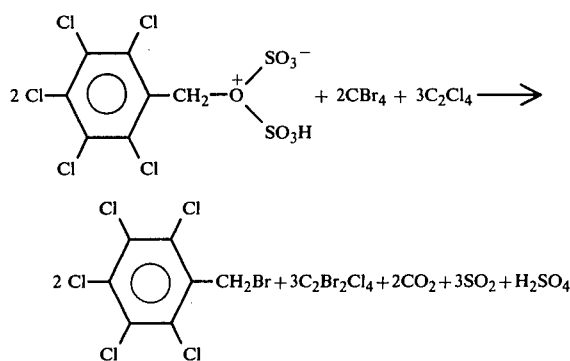

The procedure of Example 36 was repeated, except that a solution of 35.0 g (0.11 mole) of carbon tetrabromide in 100 ml. of tetrachloroethylene was substituted for carbon tetrachloride. Workup by the same procedure yielded, after evaporation of the solvent, 64.6 g of a yellow, crystalline material, subsequently shown to be a mixture of α-bromo-2,3,4,5,6-pentachlorotoluene (pentachlorobenzyl bromide) and 1,2-dibromotetrachloroethane. The yield of these materials thus amounted to 94.5%. Repeated recrystallization from ethanol yielded the benzyl bromide as the less soluble component, mp. 109.5–112.5, undepressed by mixed melting point of an authentic sample. Infrared maxima occurred at 1535, 1430, 1326, 1291, 1236, 1225, 1122, 955, 887, 871, 758, 732, 695, 678, 650, 558 and 485 cm$^{-1}$, in tetrachloroethylene and carbon disulfide solution. Its nuclear magnetic resonance spectrum in deuteriochloroform solution presented a singlet at 4.74 ppm.

Calculated for C$_7$H$_2$BrCl$_5$: C, 24.49; H, 0.58; Br, 23.28; Cl, 51.64%; Found: C, 22.4; H, 0.6; Br, 23.2; Cl, 51.6%.

The mother liquor of the recrystallization was evaporated to dryness and the residue dissolved in pentane, treated with charcoal, filtered and recrystallized from methanol to yield white crystals, melting with decomposition at 138° C. Its infrared spectrum showed maxima at 810, 760, 720, 636 and 615 cm$^{-1}$.

Calculated for C$_2$Br$_2$Cl$_4$: mol. wt. 325.67: C, 7.38; Br, 49.07. Found: mol. wt. 330, by vapor pressure osmometry in chloroform solution C, 7.38; Br, 45.8%

EXAMPLE 40

Preparation α-iodo-2,3,4,5,6-pentachlorotoluene

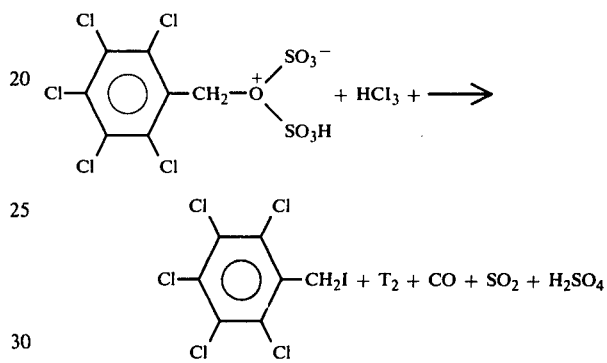

Repeating the procedure of Example 36 except that a saturated solution of a slight excess of iodoform in methylene chloride was substituted for carbon tetrachloride, resulted, after a similar workup, in the isolation of a pure sample of the title compound, called also pentachlorobenzyl iodide, in form of light yellow glistening flakes, which after recrystallization from cyclohexane, had mp 138.5°–140.5° C. Its infrared spectrum contained maxima at 1540, 1424, 1360, 1318, 1232, 1160, 1119, 1104, 953, 836, 756, 729, 678, 512 and 478 cm$^{-1}$, while the resonance of the benzylic protons in its nuclear magnetic resonance spectrum occurred at 4.65 ppm in deuteriochloroform solution.

Calculated for C$_7$H$_2$Cl$_5$I: C, 21.54; H, 0.52; Cl, 45.42; I, 32.51. Found: C, 21.6; H, 0.5; Cl, 45.4; I, 32.5%.

EXAMPLE 41

Preparation of α,α′,2,3,5,6-hexachloro-p-xylene

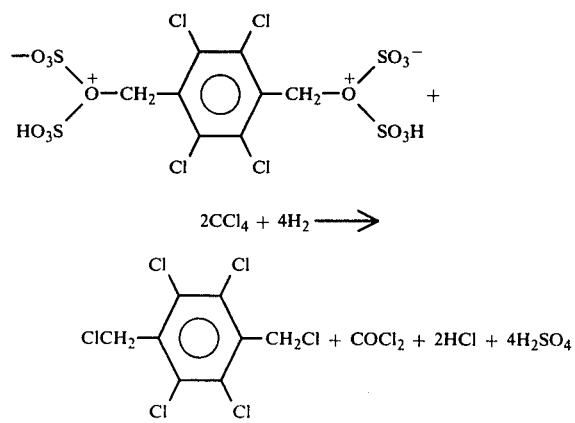

Repeating the procedure illustrated in Example 36 with the pasty residue of Example 9 resulted in the isolation of 30.3 g of yellow solids, which after recrystallization from carbon tetrachloride yielded white crystals, mp 179°-182°, in 28.1 g yield. Infrared, nuclear magnetic resonance, elemental analysis and mixed melting point showed that the product of this reaction was the title compound, which was obtained in 90% yield. Its infrared peaks occurred at 1436, 1372, 1362, 1269, 1251, 1147, 914, 837, 745, 685, 660, 632, 609, 490 and 460 cm$^{-1}$, and its nuclear magnetic resonance spectrum displayed the benzylic protons as a singlet at 4.89 ppm in deuteriochloroform solution.

Calculated for $C_8H_4Cl_6$: C, 30.71; H, 1.29; Cl, 68.00%. Found: C, 30.6; H, 1.3; Cl, 68.2%.

EXAMPLE 42

Preparation of α,α',2,4,5,6-hexachloro-m-xylene

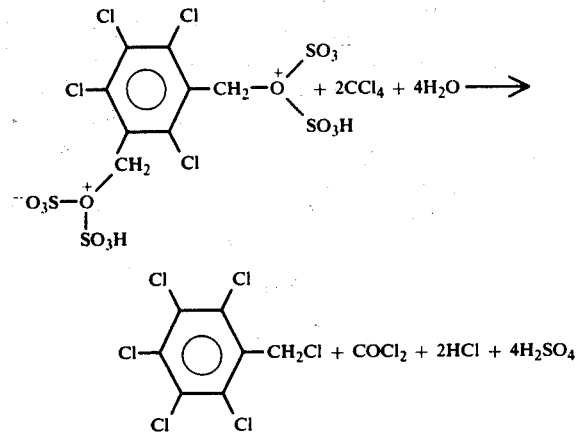

Repeating the procedure of Example 41 with the residue obtained in Example 10 resulted in the isolation of the title compound, mp 136°-138° C. in 92% yield. Spectral parameters: infrared, 1555, 1448, 1398, 1376, 1278, 1268, 1160, 1129, 1010, 932, 910, 906, 770, 752, 730, 682, 618, 608, 604, 540, 530, 446 and 436 cm$^{-1}$; nuclear magnetic resonance absorption at 4.86 ppm in CDCl$_3$ solution.

Calculated For $C_8H_4Cl_6$: C, 30.71; H, 1.29; Cl, 68.00%. Found: C, 30.5; H, 1.3; Cl, 68.3%.

EXAMPLE 43

Preparation of α,α',3,4,5,6-hexachloro-o-xylene

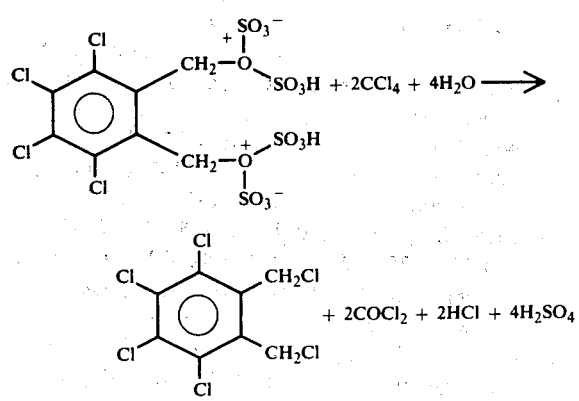

When the procedure of Example 41 was repeated except that the reaction with carbon tetrachloride was carried out with the product of Example 11, a 94% yield of the title compound was realized. After recrystallization from methanol the pure compound had mp 84.0°-84.7° C.; infrared maxima were found at 2998, 2898, 1550, 1480, 1450, 1400, 1375, 1278, 1270, 1240, 1196, 1153, 951, 940, 890, 723, 716, 692, 612, 609, 532 and 462 cm$^{-1}$, ran in $C_2Cl_4$ and $CS_2$ solutions; nuclear magnetic resonance peak as a singlet occurred at 4.85 ppm in deuteriochloroform solution.

Calculated for $C_8H_4Cl_6$: C, 30.71; H, 1.29; Cl, 68.00%. Found: C, 30.7; H, 1.3; Cl, 67.8%.

EXAMPLE 44

Preparation of 2,3,5,6-tetrabromo-α,α'-dichloro-p-xylene.

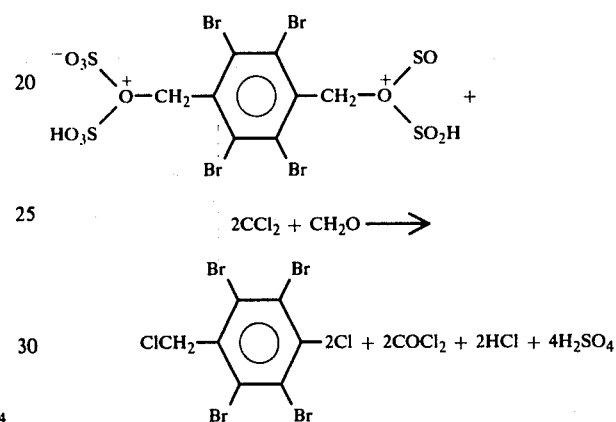

Repeating the procedure of Example 41 except that the product of Example 12 was used to react with carbon tetrachloride, a nearly quantitative yield of the title compound, mp 232°-233° C. was obtained. Its infrared maxima were at 1435, 1350, 1330, 1265, 1237, 1134, 1104, 904, 740, 625, 597 and 544 cm$^{-1}$: nuclear magnetic resonance displayed the benzylic protons as a singlet at 5.11 ppm in deuteriochloroform solution.

EXAMPLE 45

Preparation of α,α',2,3,5,6-hexabromo-p-xylene

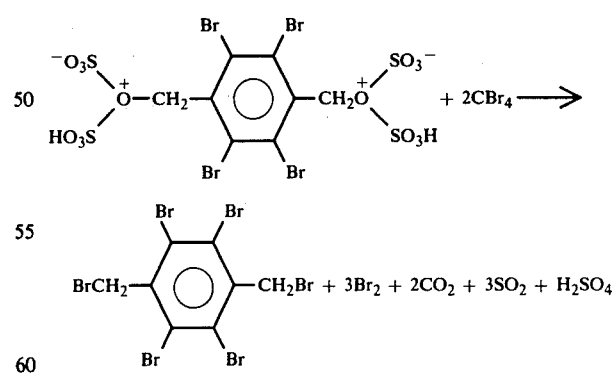

Repeating the procedure of the previous Example except that an excess of carbon tetrabromide, instead of carbon tetrachloride, was added to the dioxonium compound, a 90% yield of the title compound was obtained, mp 207.5°-270.8° C. Characteristic maxima in its infrared spectrum occurred at 1104, 868 and 638 cm$^{-1}$, the paucity of the bands being due to the poor solubility of the compound in infrared solvents. Its nuclear magnetic resonance singlet of the benzylic protons was found at 4.79 ppm in CDCl$_3$ solution.

Calculated for C$_8$H$_4$Br$_6$: C, 16.52; H, 0.70; Br, 82.78%. Found: C, 16.4; H, 0.6; Br, 82.1%.

EXAMPLE 46

Preparation of 2,3,4,5,6-pentachlorodiphenylmethane

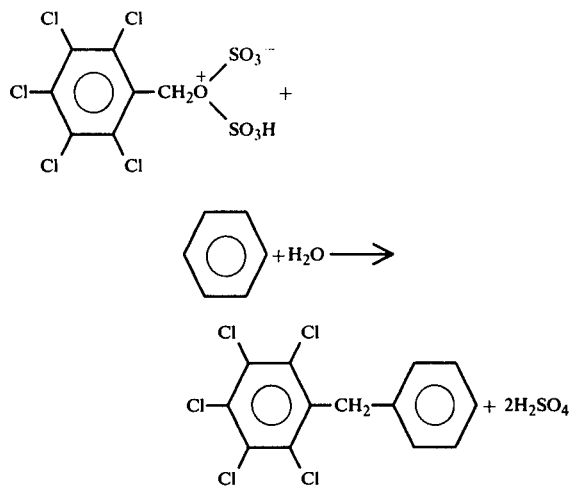

The addition of the oxonium compound prepared in Example 1 to 200 ml of benzene, with cooling and stirring, followed by the addition of water, separation of the two layers and stripping of the excess of benzene resulted in the isolation of a light brown solid, 28.8 g, which, after recrystallization from ethanol and hexane, yielded white needles, mp 112.5°–113.5° C. Elemental analysis, infrared and nuclear magnetic resonance indicated that the product of this reaction is the pentachlorodiphenylmethane indicated in the title. The yield, accordingly, was 83%. The infrared maxima occurred at 3075, 3052, 3022, 2928, 2840, 1601, 1542, 1495, 1450, 1438, 1360, 1352, 1337, 1310, 1282, 1230, 1180, 1118, 1112, 1072, 1038, 946, 884, 776, 726, 692, 678, 638, 618, 602, 540, 522 and 448 cm$^{-1}$ in C$_2$Cl$_4$ and CS$_2$ solution. The methylene protons in the nuclear magnetic resonance scan in CDCl$_3$ solution were at 4.37 ppm as a singlet and the aromatic protons at 7.18 ppm as multiplets in the correct 2:5 area ratio.

Calculated for C$_{13}$H$_7$Cl$_5$: C, 45.85; H, 2.07; Cl, 52.07%. Found: C, 45.9; H, 2.1; Cl, 51.1%.

EXAMPLE 47

Preparation of 2,3,5,6-tetrachloro-α,α'-diphenyl-p-xylene

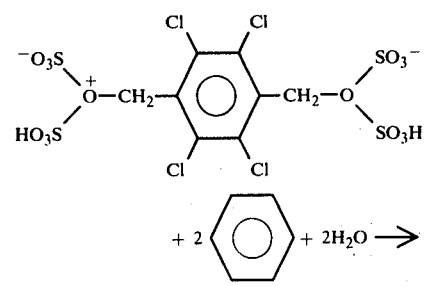

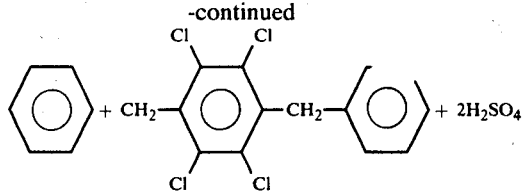

When the dioxonium compound prepared in Example 9 was added portionwise and with cooling to an excess (200 ml) of benzene and the reaction mixture was worked up as in the preceding example, there was obtained 21.6 g of a yellow solid, which after recrystallization from carbon tetrachloride, had up 179.5°–181.0° C. Infrared, nuclear magnetic resonance and elemental analysis confirmed its structure as that indicated in the title of this example. The infrared parameters, run in C$_2$Cl$_4$ and CS$_2$ solutions, were at 3075, 3052, 3022, 2922, 2835, 1600, 1498, 1452, 1430, 1390, 1370, 1282, 1250, 1158, 1133, 1100, 1072, 1029, 932, 883, 729, 693, 654, 618, 580, 524, 500 and 447 cm$^{-1}$. The benzylic hydrogens were found to resonate in CDCl$_3$ solution at 4.41 ppm and the aromatic protons at 7.20 ppm (as multiplets) in the correct 2:5 area ratio.

Calculated for C$_{20}$H$_{14}$Cl$_4$: C, 60.60; H, 3.53; Cl, 35.87%. Found: C, 60.7; H, 3.6; Cl, 35.7%.

EXAMPLE 48

Preparation of 2-chloro-3-pentachlorophenylpropanoic acid

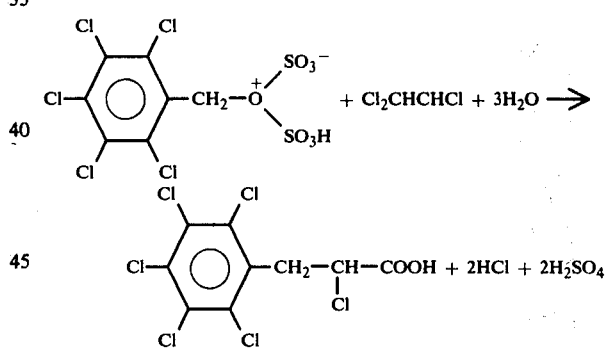

When the procedure of Example 1 was repeated and an excess (100 ml) of trichloroethylene was added to the resultant oxonium compound with cooling and stirring. After circa 20 minutes of reaction time the mixture was poured into water and the excess of solvent was removed under vacuum from the organic phase. There was obtained 34.2 g of a white solid, which after recrystallization melted at 170.0°–172.5° C. Its infrared spectrum in mineral oil mull had maxima at 1722, 1424, 1350, 1318, 1292, 1268, 1230, 1195, 1168, 1118, 1058, 956, 943, 928, 890, 775, 765, 724, 690, 680, 632, 628, 598, 514 and 497 cm$^{-1}$, and its nuclear magnetic resonance spectrum in DMSO solution displayed the benzylic protons as a doublet at 3.66 ppm and the single proton adjacent to the carboxyl as a triplet at 4.77 ppm, with J being 7 cps.

Calculated for C$_9$H$_4$Cl$_6$O$_2$: C, 30.29; H, 1.13; Cl, 59.63. Found: C, 30.1; H, 1.1; Cl, 59.2%.

EXAMPLE 49

Preparation of 2-chloro-3-pentachlorophenylpropanoic acid

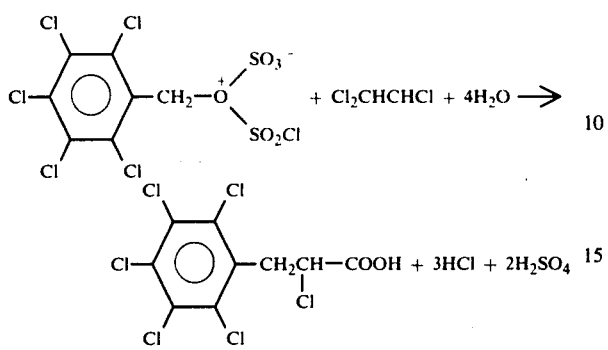

To the oxonium compound produced in Example 3 there was added 10 ml of sulfuric acid prior to the addition of trichloroethylene (150 ml), which was carried out with cooling by ice. Workup as in the preceding example resulted in the isolation of 35.6 g (quantitative yield) of the acid identical with that of the preceding example.

EXAMPLE 50

Preparation of 2,3,5,6-tetrachloro-p-benzene bis(2-chloropropionic acid)

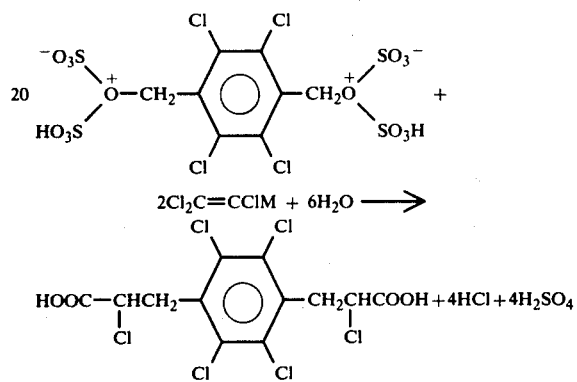

When the dioxonium compound prepared in Example 9 was mixed with 20 ml of concentrated sulfuric acid and the resultant mixture was added to 100 ml of trichloroethylene, followed by stirring at room temperature for one hour and heating to reflux for another hour, treatment with ice, separation, drying and removal of the excess of solvent by stripping under reduced pressure, there was obtained 42.3 g of the title compound corresponding to 99% yield, melting, after recrystallization from ortho-chlorotoluene, between 240° and 250° C., with decomposition. Its nuclear magnetic resonance spectrum ran in hexadeuterioacetone, showed the benzylic protons as a doublet at 3.85 ppm and the adjacent proton as a triplet at 4.88 ppm, with a coupling constant of 8 cps.

Calculated for $C_{12}H_8Cl_6O_4$: C, 33.57; H, 1.87; Cl, 49.58%. Found: C, 33.5; H, 2.0; Cl, 47.1%.

The reaction of the dioxonium compound with trichloroethylene is visualized as an addition (or insertion) reaction involving again an oxonium compound (50A) represented by the following equation

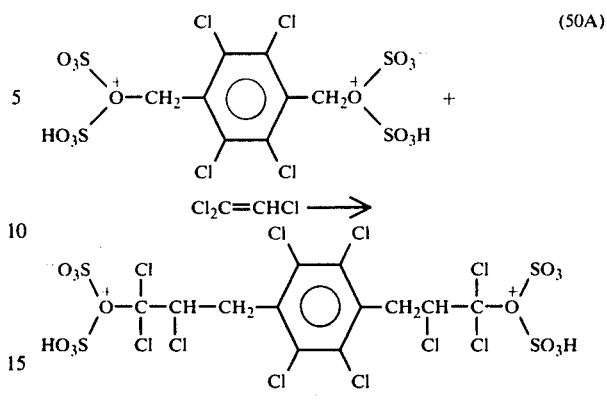

Support for the structure of 50A was obtained from its nuclear magnetic resonance spectrum, which was run prior to its hydrolysis to the dipropionic acid named in the title. The nuclear magnetic resonance spectrum of 50A in trichloroethylene solution contained the benzylic protons as a doublet at 4.39 ppm, the adjacent single proton as a triplet at 5.58 ppm with a coupling constant of 7 cps; and the acidic protons as a singlet at 5.03 ppm. Hydrolysis of 50A to the title product involves the transformation of the geminal chlorines into a carbonyl function, thus yielding the organic acid end product.

EXAMPLE 51

Preparation of 2,4,5,6-tetrachloro-m-benzene bis(2-chloropropionic acid)

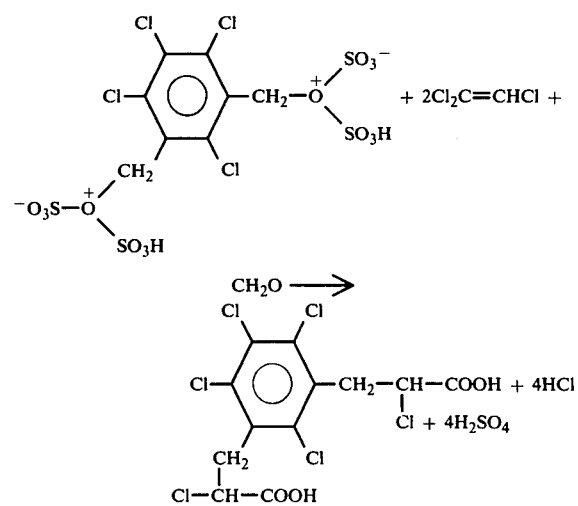

Repeating the procedure of the preceding example with the dioxonium compound obtained in Example 10, there was obtained a quantitative yield, 42.9 g of the title compound, mp 196°–199° C. Its infrared contained maxima in Nujol mull at 1730, 1692, 1330, 1288, 1279, 1252, 1212, 1172, 1110, 965, 955, 929, 780, 750, 720, 700, 603, 54 and 470 cm$^{-1}$ and its nuclear magnetic resonance spectrum, run in hexadeuterioacetone, displayed the benzylic protons as a doublet at 3.78 ppm, the adjacent single proton as a triplet at 4.83 ppm, with a coupling constant of 8 cps.

Calculated for $C_{12}H_8Cl_6O_4$: C, 33.57; H, 1.87; Cl, 49.58%. Found: C, 33.9; H, 210; Cl, 49.6%.

EXAMPLE 52

Preparation of 3,4,5,6-tetrachloro-o-benzene bis(2-chloropropionic acid

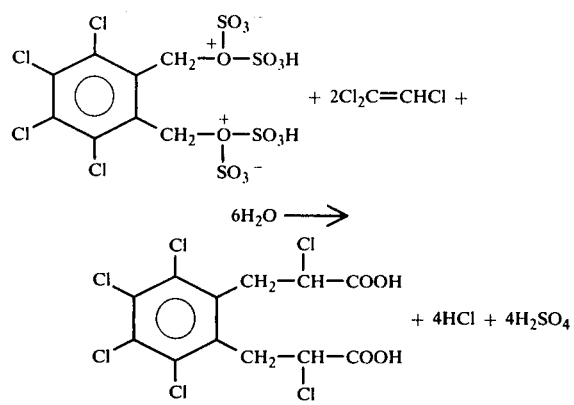

Repeating the procedure of Example 50, except that the dioxonium compound obtained in Example 11 was utilized, there was obtained 27.0 g or 63% of the title compound, mp 250°-252° recrystallized from diethyl ether. Its infrared spectrum, obtained as a mineral oil mull, had maxima at 1750, 1724, 1370, 1308, 1268, 1225, 1172, 1150, 1055, 942, 805, 745, 698, 663, 620 and 538 cm$^{-1}$ and its nuclear magnetic resonance spectrum which was complex, showed the four benzylic protons at 3.8 ppm, the adjacent protons at 4.7 ppm.

Calculated for $C_{12}H_8Cl_6O_4$: C, 33.57; H, 1.87% Found: C, 33.7; H, 1.9%.

EXAMPLE 53

Preparation of 2,4,5,6-tetrabromo-m-benzene bis(2-chloropropionic acid)

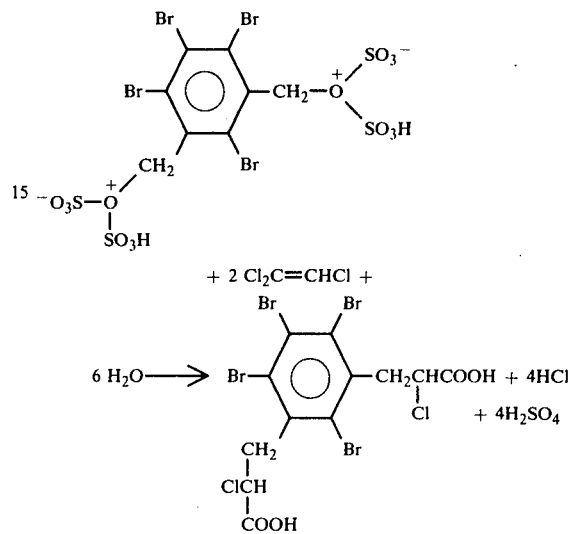

Applying the procedure described in Example 50 to the dioxonium compound obtained in Example 13, resulted in the formation and isolation of the title compound, mp 205°-212°, in 36.4 g or 60% yield.

EXAMPLE 54

Preparation of 2,3,5,6-tetrachloro-p-benzene bis(2-chloropropionic acid

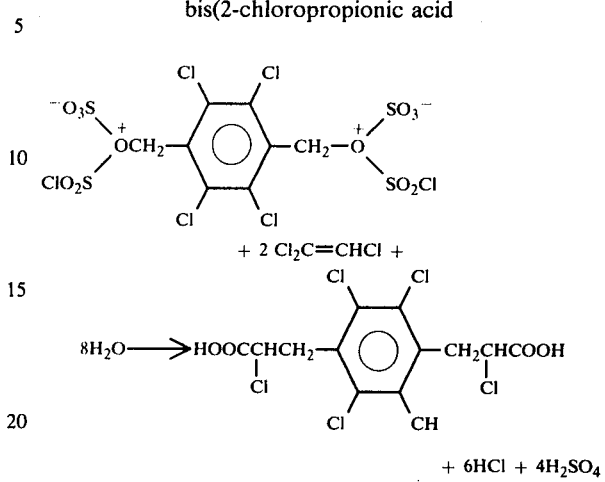

Repeating the procedure of Example 50 with the dioxonium compound obtained in Example 18 resulted in the essentially quantitative formation (42.0 g) of the title compound, found to be identical with the product characterized in Example 50.

EXAMPLE 55

Preparation of 2,2-dichloro-3-phenylpropanoic acid

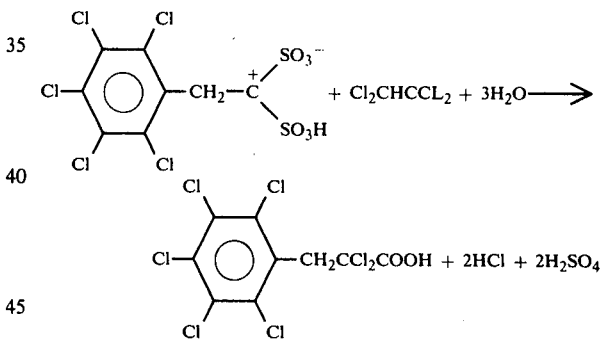

When the procedure of Example 48 was repeated, except that tetrachloroethylene, instead of trichloroethylene, was added to the oxonium compound, workup as described, resulted in the isolation of 40.0 grams of an off white solid. Its nuclear magnetic resonance spectrum indicated the presence of 5% of pentachlorobenzyl chloride, 3% of 2-chloro-3-pentachloro-phenyl propenoic acid and 92% of the title compound. Trituration with hexane and recrystallization from benzene yielded white crystals, mp 173°-176°, shown by infrared, nuclear magnetic resonance and elemental analysis to be the pure title compound. Its infrared spectrum, obtained as a mineral oil mull, had maxima at 1722, 1425, 1360, 1325, 1262, 1250, 1230, 1112, 1042, 979, 958, 932, 864, 774, 725, 700, 672, 653, 640, 600, 542, 520 and 460 cm$^{-1}$; its nuclear magnetic resonance run in DMSO, displayed the benzylic protons as a singlet at 4.31 ppm.

Calculated for $C_9H_3Cl_7O_2$: C, 27.64; H, 0.77; Cl, 63.43%. Found: C, 27.8; H, 0.8; Cl, 63.5%.

EXAMPLE 56

Preparation of α, 2,3,4,5,6-hexachlorocinnamic acid

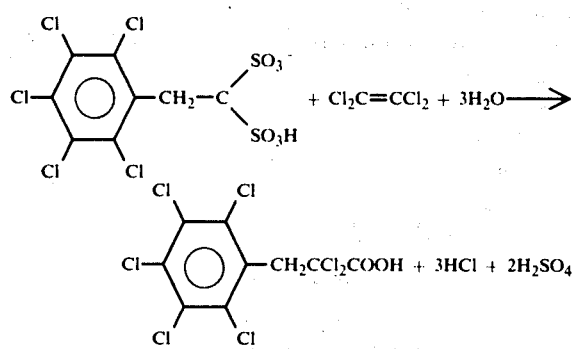

When the procedure of the preceding example was repeated, but the tetrachloroethylene solution was heated to reflux for half an hour, workup as before yielded 28.0 g of a crude product, whose nuclear magnetic resonance spectrum, ran in hexadeuterioacetone, indicated the presence of both the propenoic acid (major) and the propanoic acid. Recrystallization from tetrachloroethylene yielded 23.1 g (68% yield) of the pure title compound, mp 242°-243° C. Its infrared spectrum in Nujol mull had maxima at 1715, 1698, 1525, 1426, 1348, 1328, 1300, 1260, 1241, 1220, 1125, 1032, 955, 908, 868, 790, 754, 740, 722, 696, 672, 628, 588, 540 and 484 cm$^{-1}$; and its nuclear magnetic resonance spectrum displayed the olefinic proton at 7.89 ppm in deuterioacetone solution.

Calculated for $C_9H_2Cl_6O_2$: C, 30.05; H, 0.57; Cl, 59.95%. Found: C, 30.4; H, 0.6; Cl, 60.1%.

EXAMPLE 57

Preparation of α, 2,2,3,3,4,5,6,7-nonachloro-1-indanacetic acid.

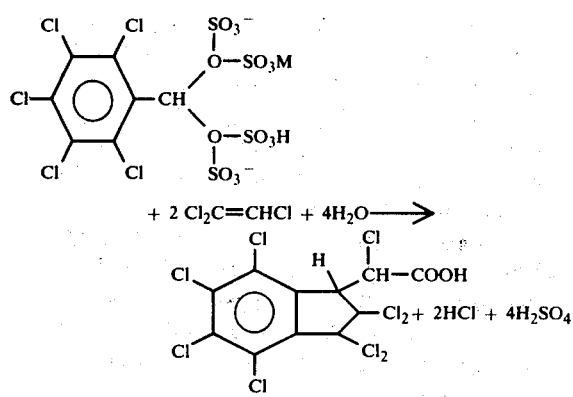

When an excess (125 ml) of trichloroethylene was added to the dioxonium compound prepared in Example 6 and the resultant mixture was heated at 60° C. for a period of 30 minutes, followed by adding it to water, separating and drying the organic phase with anhydrous calcium sulfate, filtrating and stripping under reduced pressure in a rotating evaporator, there was obtained 42.6 g of an orange oil. Trituration with hexane yielded 22.1 g or 45.5% of the title compound, which after recrystallization from benzene, had mp 214-216° C. Its infrared spectrum contained maxima at and its nuclear magnetic resonance spectrum in hexadeuterioacetone displayed an AB quartet at 5.46 and 6.45 ppm, with J = 11 cps.

Calculated for $C_{11}H_3Cl_9O_2$ : C, 27.16; H, 0.62; Cl, 65.62%. Found : C, 27.7; H, 0.7; Cl, 62.1%.

EXAMPLE 58

Preparation of 1,1,2,2,4,5,6,7-octachloroindan

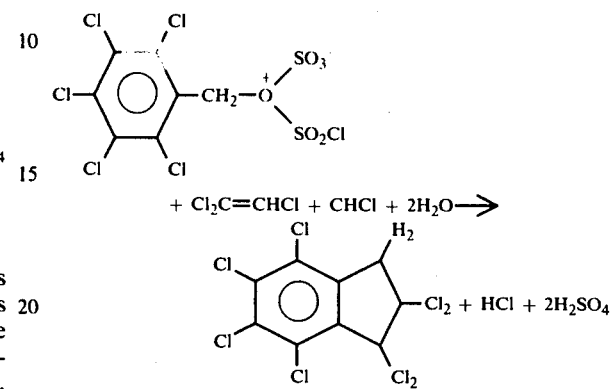

The oxonium compound of Example 3 was prepared. The excess of sulfur trioxide was stripped under reduced pressure to a pot temperature of 40° C. at 5 mmHg and the residue was cooled to 10° C. Trichloroethylene (100 ml) was added in one portion and after the exothermic reaction was over, the resultant mixture was stirred for 15 minutes, poured onto ice and most of the solvent was stripped from the organic phase under reduced pressure. Filtration of the thick slurry yielded 39.4 g or a quantitative yield of the title compound, which after recrystallization from benzene had mp 145.5-147.0° C. Its infrared spectrum displayed maxima in Nujol mull at 1380, 1304, 1242, 1230, 1188, 1120, 968, 932, 918, 793, 745, 725, 680, 658, 555, 518 and 480 cm$^{-1}$; and its nuclear magnetic resonance spectrum showed the benzylic protons as a single peak at 4.38 ppm in DMSO solution and at 3.71 ppm in hexadeuteriobenzene solution.

Calculated for $C_9H_2Cl_8$ : C, 27.50; H, 0.51; Cl, 72.0%. Found : C, 28.1; H, 0.7; Cl, 71.4%.

EXAMPLE 59

Preparation of 1,1,2,2,4,5,5,6,6,8-decachloro-1,2,3,5,6,7-hexahydro-s-indacene

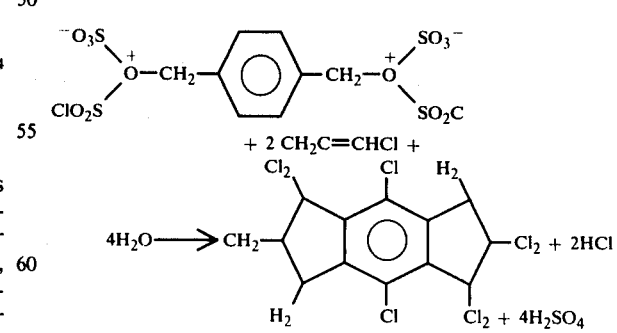

When the procedure of the preceding example was carried out with the dioxonium compound prepared in Example 18, there was obtained 50.3 g or a quantitative yield of the title compound, mp 175.5-177.0° C., after recrystallization from benzene. Its infrared spectrum in tetrachloroethylene and carbon disulfide solution contained maxima at 1600, 1430, 1374, 1308, 1257, 1180, 1140, 1108, 994, 947, 916, 852, 754, 698, 657, 617, 538, 507 and 468 cm$^{-1}$ and its nuclear magnetic resonance spectrum contained a single peak at 4.48 ppm in hexadeuterioacetone solution and at 3.77 ppm in hexadeuteriobenzene solution.

Calculated for $C_{12}H_4Cl_1O$: C, 28.66; H, 0.80; Cl, 70.52% Found : C, 29.5; H, 1.0; Cl, 69.3%.

EXAMPLE 60

Preparation of N-pentachlorobenzyl acetamide

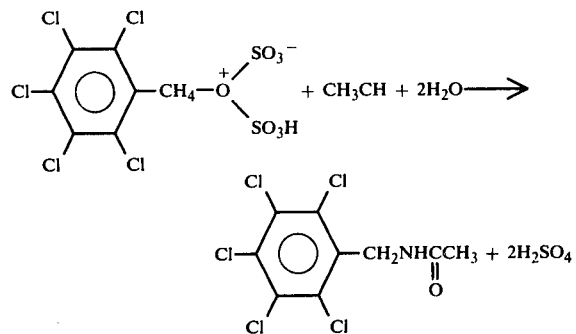

When an excess (125 ml) of acetonitrile was added at once to the oxonium compound prepared in Example 1, a vigorous reaction ensued, but was kept under control with strong cooling. After the reaction subsided, the mixture was heated to reflux and the light yellow slurry poured into water. The white powder that precipitated was filtered off and dried in the air, after which it weighed 36.0 g. Recrystallization from methanol yielded 21.3 g or 66% of the title compound, mp 223.5-224.0° C., whose structure was established by spectroscopic and elemental analyses. Its infrared spectrum from a Nujol mull had maxima at 3270, 1630, 1540, 1360, 1320, 1278, 1248, 1232, 1210, 1124, 1040, 1010, 770, 725, 682, 632, 592, 510 and 464 cm$^{-1}$; and its nuclear magnetic resonance spectrum in DMSO displayed the benzylic protons at 4.57 ppm, the methyl protons at 2.53 ppm and the NH proton at 3.32 ppm.

Calculated for $C_9H_6Cl_5NO$ : C, 33.62; H, 1.89; Cl, 55.16%. Found : C, 33.7; H, 2.0; Cl, 55.3%.

EXAMPLE 61

Preparation of N-pentachlorobenzyl acrylamide

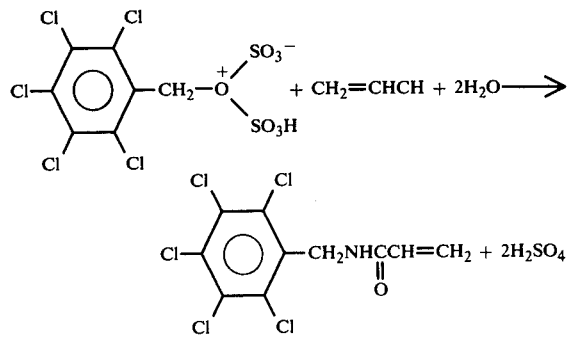

The procedure of Example 1 was exactly repeated and to the resultant oxonium compound there was added 125 ml of methylene chloride, followed by the addition of 125 ml of acrylonitrile. After the exothermic reaction subsided the resultant light yellow slurry was heated at 60° C. for 0.5 hour. Filtration yielded 12.5 g of solids, shown to be the title compound by infrared, nuclear magnetic resonance and elemental analysis. The yield was 37.5%. Recrystallization from methanol yielded crystals with mp 213-214° C. Its nuclear magnetic resonance spectrum in DMSO consisted of the vinyl proton multiplets at 6.0-6.4 and 5.5-5.7 ppm, the benzylic protons at 4.64 ppm and the amide proton at 3.34 ppm.

Calculated for $C_{10}H_6Cl_5NO$ : C, 36.01; H, 1.82; Cl, 53.19% Found : C, 36.0; H, 1.8; Cl, 53.1%.

EXAMPLE 62

Preparation of the sodium salt of trans-2-(pentachlorophenyl)ethene sulfonic acid

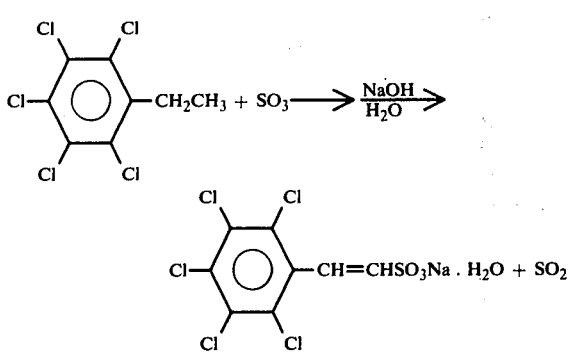

When the procedure of Example 1 was repeated with 2,3,4,5,6-pentachloroethylbenzene (mp 56-57° C.) replacing pentachlorotoluene and the reaction mixture was refluxed for five hours, stripping of the excess of sulfur trioxide yielded a dark residue which was poured into ice water. Neutralization by dilute aqueous sodium hydroxide and filtration yielded 17.5 g or 43% of theory of the title compound as the mono hydrate. Recrystallization from ethanol yielded an analytical sample, infusible below 300° C. Its nuclear magnetic resonance spectrum, run in DMSO, displayed the olefinic protons as an AB quartet at 6.73 and 6.97 ppm, with a coupling constant of 16 cps; the infrared spectrum, run in FLUOROLUBE and mineral oil mulls, contained maxima at 3580, 3506, 1610, 1375, 1340, 1304, 1190, 1062, 946, 856, 770, 718, 688, 652, 630, 600, 552, 540 and 510 cm$^{-1}$ Calculated for $C_8H_2Cl_5NaO_3S.H_2O$: C, 24.23; H, 0.51; Cl, 44.72; S, 8.09%. Found : C, 24.6; H, 0.9; Cl, 44.5, S, 8.2%.

EXAMPLE 63

Preparation of the sodium salt of pentachlorobenzene sulfonic acid

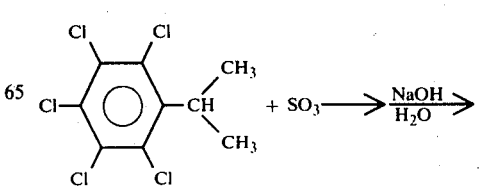

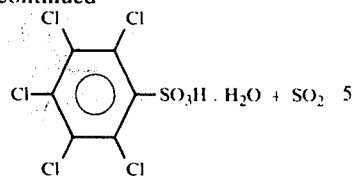

The procedure of Example 1 was repeated, except that 29.2 g of 2,3,4,5,6-pentachlorocumene (mp 78.5–80.0°; bp 106–108° C. at 0.05 mm Hg.) was substituted for the toluene. After refluxing for five hours the excess of sulfur trioxide was distilled off and the dark residue was poured onto ice, and neutralized with dilute aqueous sodium hydroxide solution. Filtration of the solids yielded a damp mud which on trituration with dioxane yielded a white powder, which was found to represent a 63% yield of the title compound containing one mole water of crystallization.

Calculated for $C_6Cl_5NaO_3S \cdot H_2O$: C, 19.45; H, 0.55; Cl, 47.86; S, 8.65%. Found : C, 19.3; H, 0.7; Cl, 46.6; S, 8.5%.

EXAMPLE 64

Preparation of 2,3,5,6-tetrachloro-p-tolualdehyde

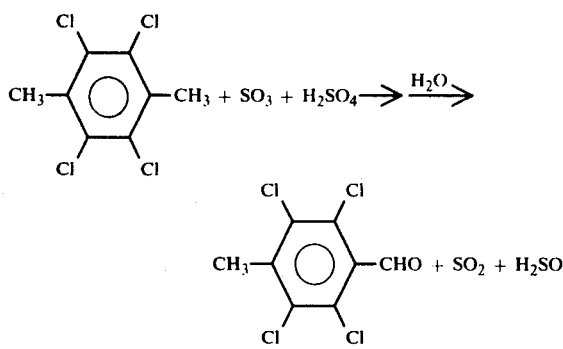

The procedure of Example 9 was repeated except that an excess of 20% fuming sulfuric acid (300 g) was used in place of pure sulfur trioxide and that heating was carried out between 90 and 100° for a period of four hours. During this time a deep purple solution was produced and strong gas evolution (acidic fumes) accompanied the heating of the reaction mixture. After cooling to room temperature the solution was added slowly to ice with good stirring. An orange-yellow precipitate formed which was filtered, washed repeatedly with water and dried in the air, yielding 24.3 g of product. Recrystallization from ethyl acetate and carbon tetrachloride yielded slightly off-white crystals, mp 200.0–206.5° C., shown by spectral and elemental analyses to be the title compound. Its infrared spectrum in tetrachloroethylene and carbon disulfide solution displayed maxima at 2855, 1720, 1350, 1244, 1230, 1140, 1027, 988, 832, 730, 696, 648, 529 and 468 cm$^{-1}$. Its nuclear magnetic resonance spectrum in deuteriochloroform consisted of two singlets: the aldehydic proton at 10.4 ppm and the methyl protons at 2.70 ppm in the correct 1:3 area ratio.

Calculated for $C_8H_4Cl_4O$: C, 37.25; H, 1.56; Cl, 54.98%. Found : C, 37.3; H, 1.6; Cl, 54.8%.

EXAMPLE 65

Preparation of 2,3,5,6-tetrachloro-p-tolualdehyde

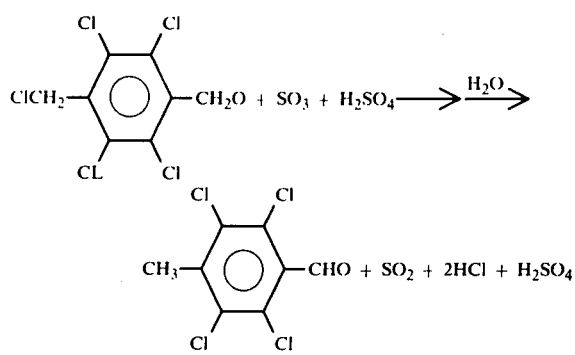

Repeating the procedure of Example 64 with α,α',2,3,5,6-hexachloro-p-xylene instead of 2,3,5,6-tetrachloro-p-xylene as the reactant yielded the title compound in 19.6 g or 76% yield.

EXAMPLE 66

Preparation of 2,3,5,6-tetrachloro-p-tolualdehyde

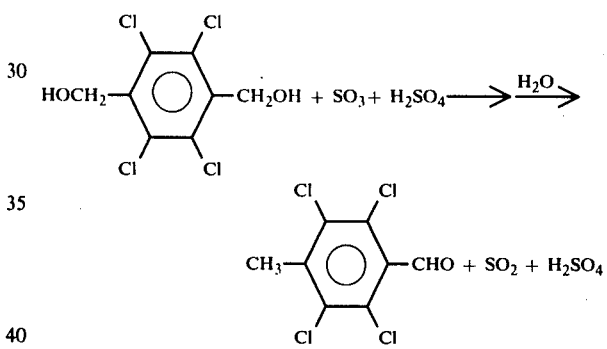

When the procedure of Example 64 was carried by replacing tetrachloro-p-xylene with an equimolar amount (27.6g) of 2,3,5,6-tetrachloro-p-xylene-α,α'-diol, a strong evolution of sulfur dioxide was observed (identified qualitatively by iodine paper), but the resultant solution did not turn purple, instead it acquired a brown amber color. After a four hour of heating period between 90 and 94° C., the clear solution was poured, after it cooled to room temperature, onto ice, yielding a yellow slurry. Since filtration was sluggish, the slurry was extracted with diethyl ether, yielding, after evaporation of the solvent 19.0 g of bright yellow solids, whose identity was determined by infrared and nuclear magnetic resonance spectra, which matched those described in Example 64.

EXAMPLE 67

Preparation of 3,4,5,6-tetrachloro-o-tolualdehyde

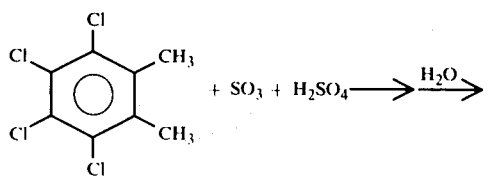

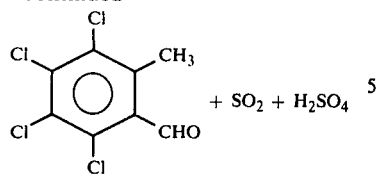 $+ SO_2 + H_2SO_4$

When the procedure of Example 64 was repeated except that tetrachloro-o-xylene was substituted for the para isomer, a 60% yield of the title compound, mp 187–194° C., was realized. Its infrared maxima occurred at 2860, 1705, 1435, 1376, 1348, 1304, 1228, 1170, 1038, 956, 894, 660 and 520 cm$^{-1}$ and its nuclear magnetic resonance spectrum in CDCl$_3$ displayed the aldehydic proton at 10.50 ppm and the methyl protons at 2.62 ppm in 1:3 area ratio.

Calculated for C$_8$H$_4$Cl$_4$O: C, 37.25; H, 1.56; Cl, 54.98%. Found: C, 37.3; H, 1.6; Cl, 53.6%.

EXAMPLE 68

Preparation of 2,3,4,5,6-pentafluorobenzyl alcohol

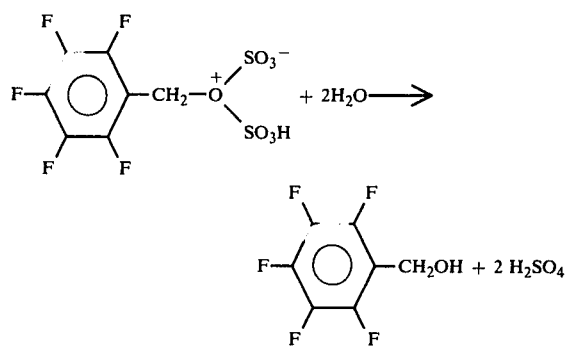

Repeating the procedure of Example 23 with the oxonium compound prepared in Example 5 resulted in the formation of a crude product in 14.9 g yield. Gas chromatography of this oil resulted in the isolation of the title compound, which was found to constitute 85% of the product, thus giving a 12.6 g or 63.5% yield. When isolated in pure form, the alcohol in CDCl$_3$ solution had nuclear magnetic resonance peaks at 4.72 and 3.85 ppm in 2:1 ratio, corresponding to the benzylic and hydroxylic protons respectively. Its infrared spectrum, run as a Nujol mull, had maxima at 3602, 3320, 1498, 1302, 1278, 1216, 1118, 1022, 948, 922, 750, 668, 598, 560 and 478 cm$^{-1}$.

EXAMPLE 69

Preparation of 2,3,5,6-tetrachloro-p-xylene-α,α'-diol

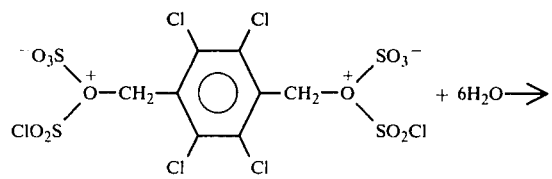

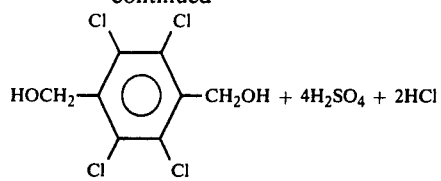 $+ 4H_2SO_4 + 2HCl$

When the procedure of Example 25 was repeated without added hydrochloric acid with the dioxonium compound prepared in Example 18 an essentially quantitative yield of the title compound was obtained. Quantitative analysis of the aqueous phase indicated the presence of four equivalent moles of sulfuric acid and two equivalent moles of hydrochloric acid, as demanded by the stoichiometry outlined above.

EXAMPLE 70

Preparation of 2,3,4,5-tetrabromo-6-chlorobenzaldehyde

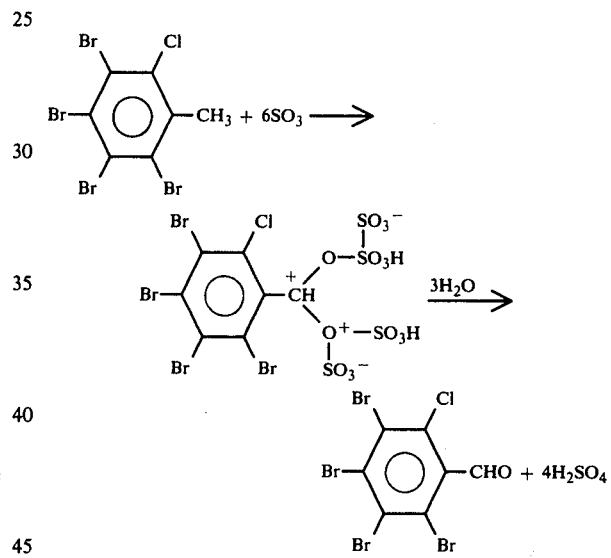

When 2,3,4,5-tetrabromo-6-chlorotoluene, mp 268–269°, was substituted for pentabromotoluene in Example 7 and the resultant dioxonium compound was hydrolyzed according to the procedure of Example 35 an essentially quantitative yield of the title compound was obtained. The structure of the novel high melting compound was confirmed by infrared and nuclear magnetic resonance spectroscopy as well as by elemental analysis.

EXAMPLE 71

Preparation of pentachlorobenzaldehyde

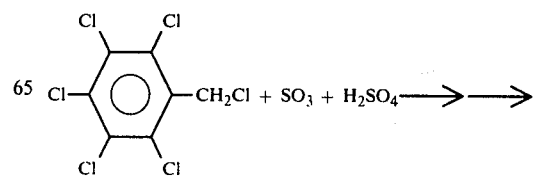

-continued

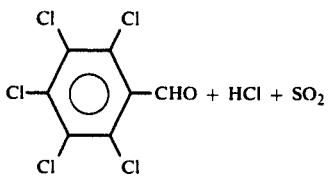 + HCl + SO₂

This example illustrates the preparation of pentachlorobenzaldehyde in an oxidation step effected by 20% oleum (fuming sulfuric acid). When pentachlorobenzyl chloride, 30.0 g (0.1 mole) was heated gradually and with good stirring, with 200 g of 20% fuming sulfuric acid, a dark green slurry was obtained. When the temperature reached 82° C., gas evolution (acidic fumes) began, which became quite copious at 85° C. For the course of two hours the color of the slurry changed to brown and after three hours of heating between 82° and 85° C. the gas evolution subsided. Heating was stopped. After cooling to room temperature the reaction mixture was added to ice, filtered, washed and dried, yielding thus 24.7 g of a light tan colored product, identified by nuclear magnetic resonance, infrared and elemental analysis as pentachlorobenzaldehyde, identical with the products described in Examples 33 and 34. The yield accordingly was 88.5% of the theoretical.

What is claimed is:

1. A process for the preparation of a compound of the formula

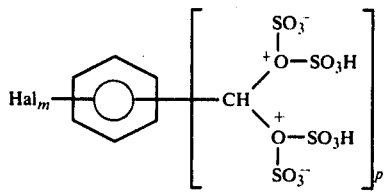

which comprises reacting an excess of neat, liquid sulfur trioxide with a compound of the formula

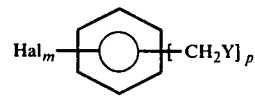

Hal is a halogen selected from the group consisting of fluorine, chlorine, bromine and iodine;
Y is hydrogen or hydroxyl;
m is 4 or 5
p is 6-m.

2. A process according to claim 1 wherein the halogen is chlorine; Y is hydrogen; and m is 5.

3. A process according to claim 1 wherein the halogen bromine; Y is hydrogen and m is 5.

4. A process according to claim 1 for the preparation of a compound of the formula

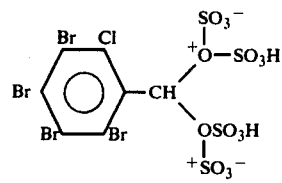

which comprises reacting an excess of neat, liquid sulfur trioxide with a compound of the formula

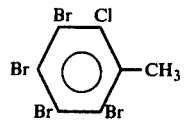

* * * * *